(12) United States Patent
Puscasu et al.

(10) Patent No.: US 7,825,380 B2
(45) Date of Patent: Nov. 2, 2010

(54) TUNABLE PHOTONIC CRYSTAL

(75) Inventors: Irina Puscasu, Somerville, MA (US);
Martin U. Pralle, Wayland, MA (US);
James T. Daly, Mansfield, MA (US);
Mark P. McNeal, Marlborough, MA (US); Edward A. Johnson, Bedford, MA (US)

(73) Assignee: Nomadics, Inc., Stillwater, OK (US)

( * ) Notice: Subject to any disclaimer, the term of this patent is extended or adjusted under 35 U.S.C. 154(b) by 0 days.

(21) Appl. No.: 12/389,239

(22) Filed: Feb. 19, 2009

(65) Prior Publication Data

US 2009/0236614 A1 Sep. 24, 2009

Related U.S. Application Data

(63) Continuation of application No. 11/177,847, filed on Jul. 8, 2005, now Pat. No. 7,498,574, and a continuation-in-part of application No. 11/156,081, filed on Jun. 17, 2005.

(60) Provisional application No. 60/586,334, filed on Jul. 8, 2004, provisional application No. 60/580,574, filed on Jun. 17, 2004.

(51) Int. Cl.
*G01J 1/00* (2006.01)

(52) U.S. Cl. .................. 250/336.1; 250/493.1; 257/98

(58) Field of Classification Search ............ 250/336.1, 250/338.1, 338.2, 338.3, 338.4, 493.1; 257/48, 257/79, 98, E33.006, E33.012
See application file for complete search history.

(56) References Cited

U.S. PATENT DOCUMENTS

| | | | |
|---|---|---|---|
| 4,245,233 A | 1/1981 | Lohstroh | |
| 5,838,016 A | 11/1998 | Johnson | |
| 5,955,749 A | 9/1999 | Joannopoulos et al. | |
| 5,973,337 A | 10/1999 | Knapp et al. | |
| 6,046,465 A | 4/2000 | Wang et al. | |
| 6,249,005 B1 | 6/2001 | Johnson | |
| 6,466,360 B2 | 10/2002 | Tokushima | |
| 6,534,798 B1 | 3/2003 | Scherer et al. | |
| 6,704,343 B2 | 3/2004 | Deng et al. | |
| 6,756,594 B2 | 6/2004 | George et al. | |
| 7,119,337 B1 | 10/2006 | Johnson et al. | |
| 7,194,174 B2 | 3/2007 | Dridi et al. | |

(Continued)

OTHER PUBLICATIONS

International Search Report under the Patent Cooperation Treaty PCT/US2005/024654, mailed Mar. 14, 2004.

(Continued)

*Primary Examiner*—David P Porta
*Assistant Examiner*—Mark R Gaworecki
(74) *Attorney, Agent, or Firm*—Foley & Lardner, LLP

(57) ABSTRACT

An infrared emitter, which utilizes a photonic crystal (PC) structure to produce electromagnetic emissions with a narrow band of wavelengths, includes a semiconductor material layer, a dielectric material layer overlaying the semiconductor material layer, and a metallic material layer having an inner side overlaying the dielectric material layer. The semiconductor material layer is capable of being coupled to an energy source for introducing energy to the semiconductor material layer. An array of surface features are defined in the device in a periodic manner or quasi-periodic. The emitter device is adapted to emit electromagnetic energy having spectral characteristics determined by parameters of the periodically distributed surface features, the parameters including shape, size, depth, distribution geometry, periodicity, material properties and defects.

37 Claims, 24 Drawing Sheets

U.S. PATENT DOCUMENTS

| | | |
|---|---|---|
| 2001/0040679 A1 | 11/2001 | Kawabata et al. |
| 2002/0051275 A1 | 5/2002 | Tokushima |
| 2002/0096492 A1 | 7/2002 | George et al. |
| 2002/0167984 A1 | 11/2002 | Scherer |
| 2003/0141507 A1 | 7/2003 | Krames et al. |
| 2004/0067163 A1 | 4/2004 | Prasad et al. |
| 2004/0125832 A1 | 7/2004 | Mahnkopf et al. |
| 2005/0151145 A1 | 7/2005 | Lin et al. |
| 2006/0151794 A1 | 7/2006 | Wierer et al. |

OTHER PUBLICATIONS

El-Kady, I., et al,; Tunable narrow-brand infrared emitters from hexagonal lattices; Photonics and Nanostructures—Fundamentals and Applications 1 (2003) 69-77; © 2003 Elsevier B.V.

Pralle, M.U., et al.; Photonic crystal enhanced narrow-band infrared emitters; Applied Physics Letters, vol. 81, No. 25, Dec. 16, 2002, pp. 4685-4687; © 2002 American Institute of Physics.

Pralle, M.U., et al.; Photonic crystals for narrow-band infrared emissions; SPIE Digital Library, 2002, vol. 4574, pp. 193 (Abstract only).

Puscasu, I., et al.; Extraordinary emission from two-dimensional plasmonic-photonic crystals; Journal of Applied Physics 98, 013531 (2005); © 2005 American Institute of Physics.

Puscasu, I.; Photonic Crystals Shrink Infrared Optical Sensors—Tracing Gases; May 2003, Spie's OE Magazine, pp. 21-23.

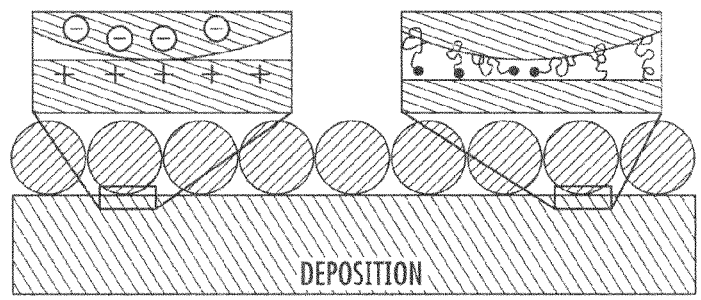
FIG. 34A DEPOSITION
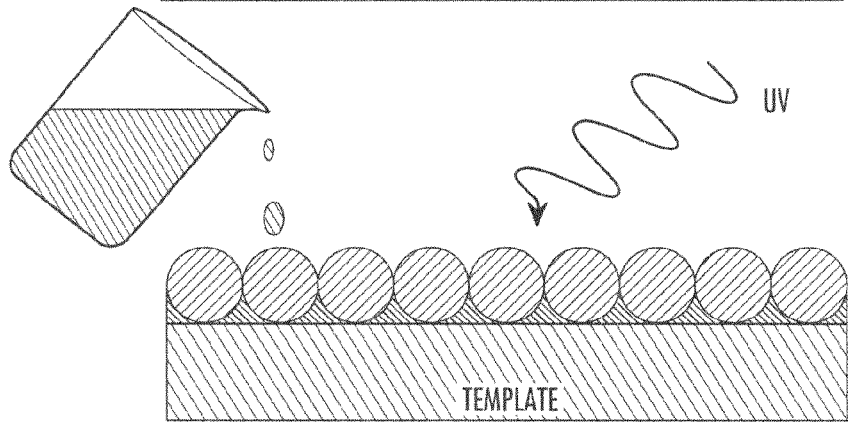
FIG. 34B TEMPLATE
FIG. 34C DEVELOP
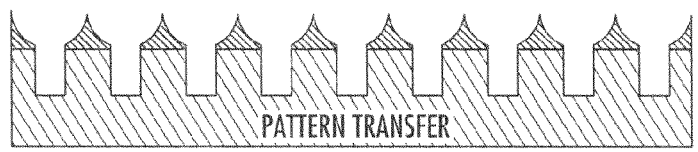
FIG. 34D PATTERN TRANSFER

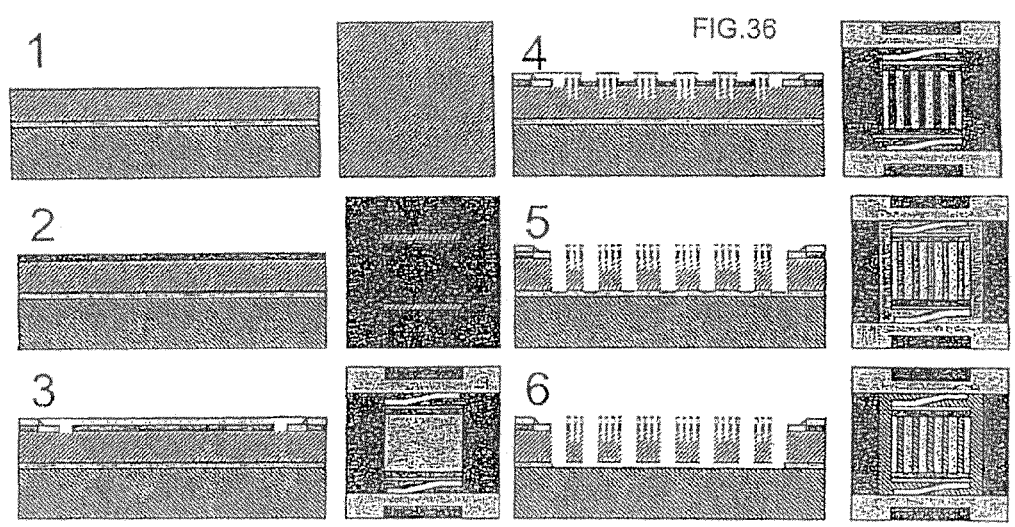

TUNABLE PHOTONIC CRYSTAL

CROSS-REFERENCE TO RELATED APPLICATION

The present application claims priority to provisional U.S. patent application Ser. No. 60/586,334, filed Jul. 8, 2004, the disclosures of which are incorporated herein by reference.

FIELD OF THE INVENTION

The present invention relates to infrared emitters/detectors/sensors for emitting and or detecting infrared electromagnetic energy, and more particularly, to micromachined devices for emitting and/or detecting infrared electromagnetic waves.

BACKGROUND OF THE INVENTION

Infrared emitters/detectors/sensors are used in many applications, for example, in detecting and discriminating the presence of specific biological, chemical substances (e.g., gases).

A conventional detector or sensor typically includes a heated element as a source of infrared emission, a filter for controlling the wavelength of emitted light, and a detector for detecting the absorption of the emitted light by a substance interacting with the emitted light. The source, referred to henceforth as an IR (infrared) emitter, typically includes a wire, filament or other infrared radiating elements. To activate, the IR emitter is heated by passing electric current through the conductive wire or filament. The current is converted to heat in the wire or filament. The infrared emission from the wire or filament is proportional to the temperature and surface area of the heated element. Often, it may be desirable to pulse the infrared emission by interrupting the electrical current periodically to modulate the surface temperature of the heated element. A spectral filter is used to selectively tailor the spectrum of the infrared emission to substantially match the absorption characteristics of the target substance to be detected.

The detector is placed facing the emitter and filter for receiving the light passed through the filter. In one example of a detector, the electrical resistance R varies as a function of its temperature T, i.e., $R=f\{T\}$. The function $f\{T\}$ may be determined empirically or analytically for a particular detector. The temperature T of the detector is dependent upon how fast it cools, and the cooling rate of the detector is dependent on the optical absorption characteristics of its immediate environment. In general, different substances (e.g., gases) are known to each exhibit distinct optical absorption characteristics. The spectral filter may be selected such that the infrared source and sensor forms a tuned cavity band emitter corresponding to the absorption characteristics of the gas under study. Thus, when the targeted gas is present in the optical path between the emitter and the detector, the optical energy received by the detector is reduced, and the temperature of the detector drops, which in turn results in changing of the resistance of the detector. Thereby, the gas is detected by monitoring the resistance R of the detector.

The thermal emissions of the current emitters used in the sensors have always been associated with a black body spectrum. Although a spectral filter is used to achieve a specific spectrum of interest, the cost of the sensing device may be high and the accuracy of the device may be reduced. Furthermore, the sensors constructed as described above are multicomponent systems requiring special alignment, calibration, and separate electronics for both the emitter and the detector making this sensors complex and expensive.

Another technique currently used is utilizing a diode laser as emission source. While this technique is highly sensitive and less subject to contamination and false alarms than electrochemical sensors, the units are expensive for home installation. In addition, because they depend on physical bandgaps, diode lasers can only be tuned with difficulty within a very narrow range.

Recently, photonic crystal structures, such as periodic dielectric arrays, have received much attention as optical and infrared filters with controllable narrow-band infrared absorbance. These photonic structures have been developed as transmission/reflection filters.

One type of device embodying a structure similar to a photonic crystal structure is disclosed in U.S. Pat. No. 5,973,316. The device includes a metallic film having apertures located therein in an array arranged in a pattern so that when light is incident on the apertures, surface plasmons on the metallic film are perturbed resulting in an enhanced transmission of the light emitted from individual apertures in the array. The light transmission properties of such an apparatus are strongly dependent upon the wavelength of the light. Enhanced transmission occurs for light wavelengths in relation to the inter-aperture spacing. The aperture array is used to filter light of predetermined wavelengths traversing the apertures. The device disclosed in U.S. Pat. No. 5,973,316 is primarily used in filters, and, generally, an external light source (emitter) is still needed to generate light that impinges onto the aperture array.

U.S. Pat. No. 6,756,594 discloses a sensor engine, which is a micromachined infrared absorption emitter/sensor, for detecting the presence of specific chemical and/or biological species. The sensor engine includes a substrate surface having a regular array of emission features disposed thereon. The substrate is made of a metallized single-crystal silicon.

A need exists for an inexpensive emitter/detector device capable of accurately emitting and/or detecting infrared light in a specific spectrum. It is desired that the device exhibits high stability over temperature.

SUMMARY OF THE INVENTION

The present invention is directed to an infrared emitter/detector/sensor for emitting and/or detecting infrared electromagnetic energy. According to one aspect of the present invention the device constructed according to the invention is utilized in devices and systems for sensing the presence of substances of interest.

The infrared emitter utilizes a photonic crystal (PC) structure to produce electromagnetic emissions with a narrow band of wavelengths. A PC structure is an artificially engineered periodic dielectric array in which the propagation of electromagnetic waves is governed by band structure-like dispersion. The structure exhibits allowed and forbidden propagation of electronic energy bands. The absence of allowed propagating electromagnetic wave modes inside the structures in a range of wavelengths called a photonic band gap, gives rise to distinct optical phenomena such as inhibition of spontaneous emission, high-reflecting omnidirectional mirrors, low-loss-waveguides, etc.

According to one preferred embodiment, the emitter includes a semiconductor material layer a dielectric material layer overlaying the semiconductor material layer, and an electrically conductive material layer having an inner side overlaying the dielectric material layer. Preferably the semiconductor material layer is made from a material selected from but not limited to a group consisting of single-crystal silicon, polysilicon, single-crystal silicon carbide (SiC), polycrystalline silicon carbide (poly-SiC), germanium, or the group III-V semiconductors, the group II-VI semiconductors including alloys of indium gallium, aluminum, arsenic, antimony, and phosphorous, and alloys of zinc, mercury, cadmium, tellurium, sulphur and selenium. SiC exhibits a high stability at high temperatures, which makes SiC a good candidate for the emitter devices according to the present invention, especially for the devices that operate in a high temperature environment. The semiconductor material layer may be doped with N type or P type impurities. The semiconductor layer on alternatively doped plastic (polymer).

According to one aspect of the present invention, the dielectric material layer is selected from but not limited to a group consisting of silicon dioxide, silicon nitride, alumina, sapphire, aluminum nitride, and silicon oxinitride.

The dielectric layer can alternatively be plastic (polymer). The electrically conductive material layer can be made from a metallic material or metallic-like material. The metallic material is preferably selected from but not limited to a group consisting of gold, aluminum, nickel, silver, titanium, and platinum, or an alloy of the above metals. The metallic-like material refers to a heavily doped semiconductor or a conductive ceramic selected from the group consisting of titanium nitride, tantalum nitride and indium tin oxide or other non-metal electrically conductive materials. The titanium nitride material allows conventional CMOS fabrication techniques to be used in the fabrication of the device according to the present invention. The electrically conductive material layer hereinafter is referred to as a metal or metallic-like material layer. Thus, the metallic-like layer can be a highly doped semiconductor with effective metallic properties or a conductive ceramic preferably made from but not limited to a group consisting of titanium nitride, tantalum nitride, and indium tin oxide. The semiconductor material layer is capable of being coupled to an energy source for introducing energy to the semiconductor material layer. The metallic material layer includes periodically distributed surface features on an outer side thereof opposite the inner side. The three material layers are adapted to transfer energy from the semiconductor material layer to the outer side of the metallic material layer and emit electromagnetic energy in a narrow band of wavelengths from the outer side of the metallic material layer. The device may have more than three or less than three layers of materials. The multi-layer structure emits electromagnetic waves with narrow peak based on their resonances.

In one preferred form, the emitted electromagnetic energy has wavelengths centered about a characteristic wavelength ($\lambda$) and has a full width at half maximum ($\Delta\lambda$), where $\Delta\lambda/\lambda$ is equal to or less than 0.5

According to one aspect of the present invention, the emitted electromagnetic energy has spectral characteristics determined by parameters of the periodically distributed surface features, the parameters including shape, size, depth, distribution geometry, periodicity, defects/artifacts, and material properties (e.g., doping paraelectric, piezoelectric).

In one preferred form, the periodically distributed surface features includes an array of holes, where the holes individually extend through at least a portion of the metallic or metallic-like material layer, or extend through the metallic or metallic-like material layer and into at least a portion of the dielectric material layer, or extend through the metallic or metallic-like material layer and the dielectric material layer, and into at least a portion of the semiconductor material layer. In another form, there is an array of holes (partially or fully through) the metallic or metallic-like layer and "the semiconductor material layer but there is no array of holes in the dielectric layer. In this form the two arrays may be aligned or in aligned, and may have the same or different geometries.

According to one aspect of the present invention, the holes have a shape selected from the group consisting of circle, n-point star, square, triangle, hexagon, donut, C and reverse C, rectangle, circle with a notch, triple-leg, and tri-bone. According to another aspect of the present invention, the array of holes are distributed in a regular geometry selected from a group consisting of parallelogram (including square, rectangular, hexagon), or in a quasi-regular geometry e.g., Archimedean tiling.

The size (i.e., diameter for circular holes), depth, and periodicity of the holes can be varied in different embodiments. In one preferred form, the holes have a diameter from about 0.5 µm to about 2.0 µm, a depth from about 1 µm to about 30 µm and a periodicity (center to center spacing between two holes) from about 1 µm to about 25 µm, but other dimensions may be employed. In one exemplary embodiment, the metal layer is about 0.1 µm thick, and the diameter of the holes is about 2 µm and the center to center spacing between two holes is about 4.2 µm.

According to one aspect of the present invention, the holes are at least partially filled with one or more materials selected from a group consisting of a dielectric material, a non-linear optical material, a liquid crystal material, a piezoelectric material, a pyroelectric material, and a ferroelectric material.

In other forms of the invention, the surface features may be "bumps" (instead of holes) according to another aspect of the present invention, the metallic or metallic-like material layer is coupled to a bias voltage and the spectral characteristics of the emitted electromagnetic energy is determined by the voltage. In another form, the semiconductor material layer is biased with a voltage, and the intensity of the emitted electromagnetic energy is determined by the voltage.

According to a further aspect of the present invention, the periodically distributed surface features include periodically distributed defects, which are structurally different from the surface features. In one preferred form, the periodically distributed defects occur at positions of every third surface feature.

According to a further aspect of the present invention, the emitted electromagnetic energy is in a conical range extending about a central axis. In one preferred form, the central axis of the conical range of emission is oblique with respect to a principal plane of the metallic or metallic-like material layer.

According to another preferred embodiment of the present invention, the emitter device includes a semiconductor layer having a metal layer deposited on the semiconductor layer. The semiconductor layer is capable of being coupled to an energy source. The device is patterned with periodically distributed surface features, preferably holes, each extending about a central axis transverse the semiconductor layer and the metal layer of the device. The configurations of the periodically distributed holes including the size, shape) depth, spacing, and distribution geometry can be the varied in different embodiments as described above. The emitted electromagnetic energy has spectral characteristics determined by parameters of the periodically distributed surface features, the parameters including shape, size, depth, distribution geometry, periodicity, defects/artifacts, and material properties (e.g., doping, paraelectric, piezoelectric).

According to a further preferred embodiment of the present invention, the device may only include one semiconductor layer, which includes periodically distributed surface features, preferred an array of holes defined on an upper surface of the semiconductor layer.

The present invention further provides an infrared spectral shifting device, which includes a plastic material layer and a metallic or metallic-like material layer overlaying the plastic material layer, the metallic or metallic-like material layer including periodically distributed surface features thereon. The infrared spectral shifting device is adapted to absorb electromagnetic energy having spectral characteristics determined by parameters of the periodically distributed surface features, the parameters including shape, size, depth, distribution geometry, periodicity, defects/artifacts, and material properties (e.g., doping, paraelectric, piezoelectric).

In one preferred form, the periodically distributed surface features are holes defined at least partially into the metallic material layer. The configurations of the periodically distributed holes including the size, shape, depth, periodicity, and distribution geometry can be the varied in different embodiments as described above.

The present invention further provides a device, which includes a dielectric material layer and a metallic or metallic-like material layer overlaying the dielectric material layer, and including periodically distributed surface features thereon. The device is adapted to emit absorb electromagnetic energy having spectral characteristics determined by parameters of the periodically distributed surface features, the parameters including shape, size, depth, distribution geometry, periodicity, defects/artifacts, and material properties (e.g., doping, paraelectric, piezoelectric). In one preferred form the periodically distributed surface features are holes defined at least partially into the metallic material layer. The configurations of the periodically distributed holes including the size, shape, depth, periodicity, and distribution geometry can be the varied in different embodiments as described above. In another preferred form, the dielectric material layer is made from a dielectric material selected from the group consisting of silicon dioxide, silicon nitride, alumina, sapphire, aluminum nitride, and silicon oxinitride.

It should be understood that various shape, size, depth, or spacing of the periodically distributed holes can be used in the present invention. The emission absorption peak wavelength and the width of the narrowband wavelengths around the peak wavelength can be adjusted by selecting the geometrical shape, size, depth, and spacing of the periodically distributed holes. In particular, the peak wavelength is linearly proportional to the periodicity of the holes and the width of the narrowband is a function of the geometrical shape, size, and depth of the holes. The peak wavelength and the width of the narrowband wavelengths around the peak wavelength also can be adjusted by selecting different materials, for example, different metals as the metal layer, by adjusting the dopant concentration in the semiconductor layer, etc.

The present invention further provides a self assembly process for defining the periodically distributed surface features. In one preferred form, the process includes forming a monolayer of microspheres on a top surface of a substrate (e.g., the emitter device having the metallic layer, the dielectric layer, and the semiconductor layer), depositing a polymer on the top surface, removing the microspheres from the top surface resulting in an array of regions uncovered by the polymer on the top surface, etching the top surface to define holes at the array of regions uncovered by the polymer, and removing the polymer from the top surface of the substrate.

BRIEF DESCRIPTION OF THE DRAWINGS

These and other features and advantages of the present invention will be better understood by reference to the following detailed description when considered in conjunction with the accompanying drawings wherein:

FIGS. 34A-34D schematically show a process for defining the periodically distributed surface features according to one preferred embodiment of the present invention;

FIG. 36 schematically shows a process for manufacturing a MEMS device embodying present invention according to one preferred embodiment of the present invention.

DETAILED DESCRIPTION OF THE PREFERRED EMBODIMENTS

The present invention is directed to an infrared emitter for emitting infrared light in a narrow band of wavelengths. The apparatus constructed according to the present invention also absorbs electromagnetic waves at the same peak wavelengths as it emits, and thereby the apparatus also can be used as an infrared detector or sensor.

Figure 1:
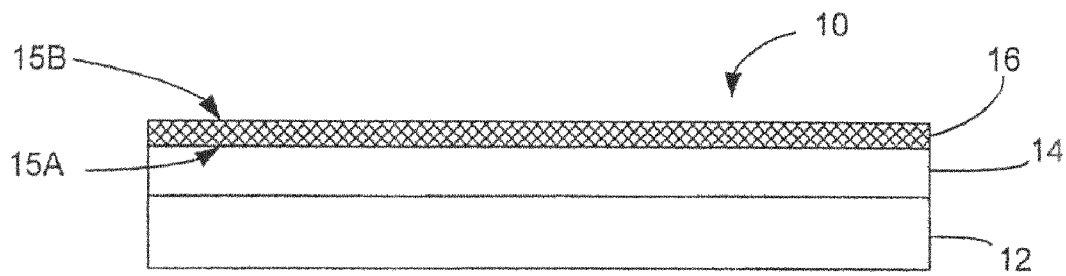
FIG. 1 is a schematic side view of a preferred embodiment of the emitter device according to the present invention.

The infrared emitter according to the present invention utilizes a photonic crystal (PC) structure to produce electromagnetic emissions with a narrow band of wavelengths. According to one preferred embodiment, as shown in FIG. 1, the emitter 10 includes a semiconductor material layer 12, a dielectric material layer 14 overlaying the semiconductor material layer 12, and an electrically conductive material layer 16 having an inner side 15A overlaying the dielectric material layer 14.

The semiconductor material layer 12 is preferably made from a material selected from but not limited to a group consisting of single-crystal silicon, polysilicon, single-crystal silicon carbide (SiC), polycrystalline silicon carbide (poly-SiC), germanium, or the group III-V semiconductors, the group II-VI semiconductors, including alloys of indium, gallium, aluminium, arsenic, antimony and phosphorous, and alloys of zinc, mercury, cadmium, tellurium, sulphur selenium, and plastics (polymer) and small molecule semiconducting organics. The semiconductor material layer 12 may be doped with N type or P type impurities. Exemplary semiconducting plastics are:

Polyphenylene
Polyphenylene vinylene
Polythiophene
Polyaniline

Any of the above dielectric plastics doped alloyed with above semiconducting plastics. Any of the above dielectric plastics doped alloyed with small molecule semiconducting organics (see below). Exemplary small molecule semiconducting organics are:

Aluminum-hydroxyquinoline complex (ALQ)
Titanylpthalocyanine

According to one aspect of the present invention, the dielectric material layer 14 is made from a material selected from, but not limited to, a group consisting of silicon dioxide, silicon nitride, alumina, sapphire, aluminum nitride, silicon oxinitride, and plastic (polymer). The electrically conductive material layer can be made from a metallic material or a metallic-like material. The metallic material preferably is selected from, but not limited to, a group consisting of gold, aluminum, nickel, silver, titanium, and platinum, tantalum, or an alloy or compound of the above metals. In addition, the metallic-like material can be a highly doped semiconductor with effective metallic properties or a conductive ceramic preferably made from but not limited to a group consisting of titanium nitride (TiN), tantalum nitride (TaN), and indium tin oxide. The electrically conductive material layer hereinafter is referred to as metal or metallic material layer. Exemplary dielectric plastics are:

Low Temp
Polystyrene (PS)
Polyethylene (PE)
Polypropylene (PP)
Poly ethyleneterapthalate (PET)
Nylon/polyesters High Temp plastics (more interesting for us) (Temp range RT-350 C):

Polyimide (PI) (Kapton)
Polyether ether ketone (PEEK)
Polyether ketone (PEK)
Polysulphone (PSO)

The device 10 may have conductors connected to the semiconductor material layer 12 or the metallic material layer 16. The semiconductor material layer 12 is capable of being coupled to an energy source for introducing energy to the semiconductor material layer 12. In one form, the semiconductor material layer 12 is coupled to an electrical current to effect resistive heating in the semiconductor material layer. Alternatively, the metallic material layer 16 is coupled to an electrical current, and the energy is transferred from the metallic material layer 16 to the semiconductor layer 12. Other methods to excite photonic resonances (to generate plasmons) can be used, such as optical pumping, electron beam pumping, or direct heating.

Figure 2:
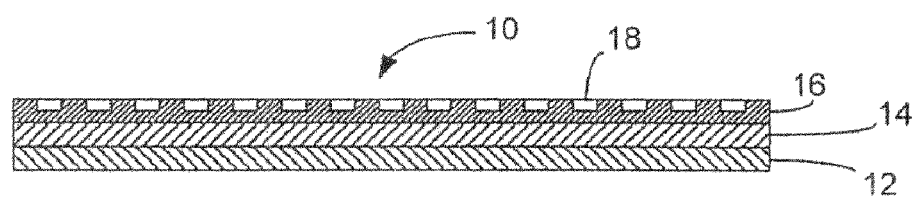
FIG. 2 is a schematic cross-sectional view of a preferred embodiment of the emitter device according to the present invention.

The metallic material layer 16 includes periodically distributed surface features on an outer side 15B thereof opposite the inner side 15A as shown in FIG. 2. The three material layers 12, 14, and 16 are adapted to transfer energy from the semiconductor material layer 12 to the outer side 15B of the material layer 16 and emit electromagnetic energy in a narrow band of wavelengths from the outer side 15B of the metallic material layer 16. The multi-layer structure emits electromagnetic waves with narrow peak based on their resonances.

In use, the semiconductor material layer 12 is stimulated. Upon stimulation, the semiconductor layer 12 emits photons. The dielectric material layer 14 couples the photons from the semiconductor material layer 12 to the inner and outer sides 15A and 15B of the metallic material layer 16. The photons excite plasmons at the metallic material layer 16. The surface plasmons at the inner and outer sides 15A and 15B of the metallic material layer 16 then decay into photons that are emitted from the outer surface 15B of the metallic material layer 16. According to one preferred embodiment, the narrow band of wavelengths emitted or absorbed by the device 10 is in infrared spectrum. According to another form, the emitted electromagnetic energy is in visible spectrum or millimeter wave spectrum.

In one preferred form, the periodically distributed surface features are void regions or holes 18 defined in the metallic material layer 16, as shown in FIG. 2, thereby to form a photonic crystal structure in the emitter device 10. According to another preferred embodiment of the present invention, the periodically distributed surface features on the outer side 15B of the metallic material layer 16 are implemented by placing dielectric material in void regions/holes 18 in the metallic material layer 16. The holes 18 may have different size, depth, shape, and inter-spacing in different embodiments. In one exemplary embodiment, the metal layer 16 is about 0.1 µm thick, and the diameter of the holes 18 is about 2 µm, and the center to center spacing between two holes is about 4.2 µm.

According a further aspect of the present invention, the surface features may include a regular array of discrete elements on the top of the emitter device. For example, a grid structure can be removed from the metallic material layer 16, leaving discrete metal islands periodically distributed on the top surface of the device 10. The surface features may have any of the shapes described above (but are complimentary).

Figure 3:
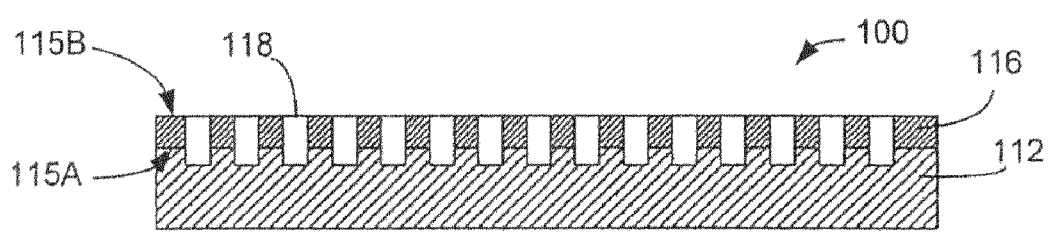
FIG. 3 is a schematic cross-sectional view of another preferred embodiment of the emitter/detector according to the present invention.

FIG. 3 illustrates another preferred embodiment 100 of the present invention, which only includes a semiconductor layer 112 and a metal layer 116 deposited on the semiconductor layer 112. The semiconductor layer 112 is capable of being coupled to an energy source. The metal layer 116 includes an inner surface 115A and an outer surface 115B. The inner surface 115A is the surface in contact with the semiconductor layer 112. The material of the semiconductor layer 112 and the metal layer 116 are the same as the semiconductor layer and the metal layer in device 10 as described above. The metal layer 116 includes periodically distributed surface features 118 on the outer surface 115B. The configurations of the periodically distributed surface features 118 including the size, depth, shape, spacing, and distribution geometry can be the same as described in the embodiment 10 shown in FIG. 2. For example, the periodically distributed surface features can be substantially circular holes defined through the metal layer 116 and into a portion of the semiconductor layer 112, as shown in FIG. 3.

Figure 4:
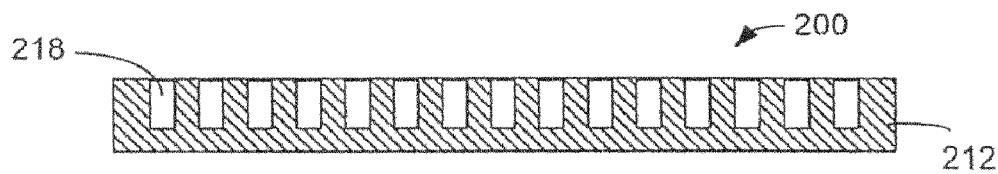
FIG. 4 is a schematic cross-sectional view of a further preferred embodiment of the emitter device according to the present invention.

FIG. 4 illustrates a further embodiment of the present invention, in which the device 200 only includes one semiconductor layer 212. The semiconductor layer 212 is capable of being coupled to an energy source. The semiconductor layer 212 includes periodically distributed surface features 218 on an upper surface. The configurations of the periodically distributed surface features including the size, shape, depth, spacing, and distribution geometry can be the same as described in the embodiments shown in FIGS. 2 and 3. For example, the periodically distributed surface features can be substantially circular holes defined at least partially through the semiconductor layer 212, as shown in FIG. 4.

The embodiments shown in FIGS. 2-4 have a similar or same structure, and therefore, in the following description, only one embodiment is used for detail description, however, a person skilled in the art should understand the same properties or characteristics should apply to the other embodiments. For example, detail descriptions for the holes 18 may also apply to the holes 118 in FIG. 3 and the holes 218 in FIG. 4.

Figure 5:
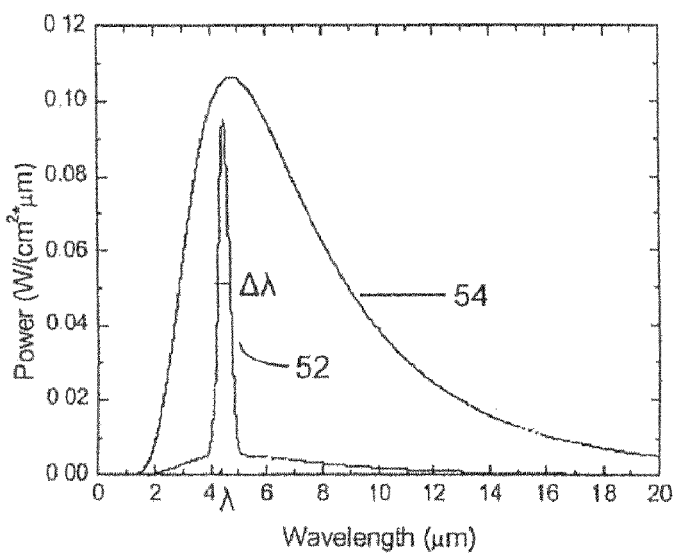
FIG. 5 shows a diagram of spectral characteristics of the emitted electromagnetic energy from the emitter device according to the present invention compared with emission from a blackbody.

FIG. 5 schematically plots a spectrum of the emitted electromagnetic energy from the emitter device according to the present invention compared to a broadband emission from a blackbody. As shown in FIG. 5, the curve of the emitted electromagnetic as indicated by reference number 52 has a narrow band peak emission compared to a blackbody emission as indicated by reference number 54. In one preferred form, the emitted electromagnetic energy has wavelengths centered about a characteristic wavelength ($\lambda$) and having a full width at half maximum ($\Delta\lambda$) where $\Delta\lambda/\lambda$ is preferably equal to or less than 0.5. The center wavelength ($\lambda$) is primarily defined by the spacing of the periodically distributed surface features and the full width at half maximum ($\Delta\lambda$) is primarily defined by the size, shape, and depth of the periodically distributed surface features, and defects/artifacts.

Figure 6:
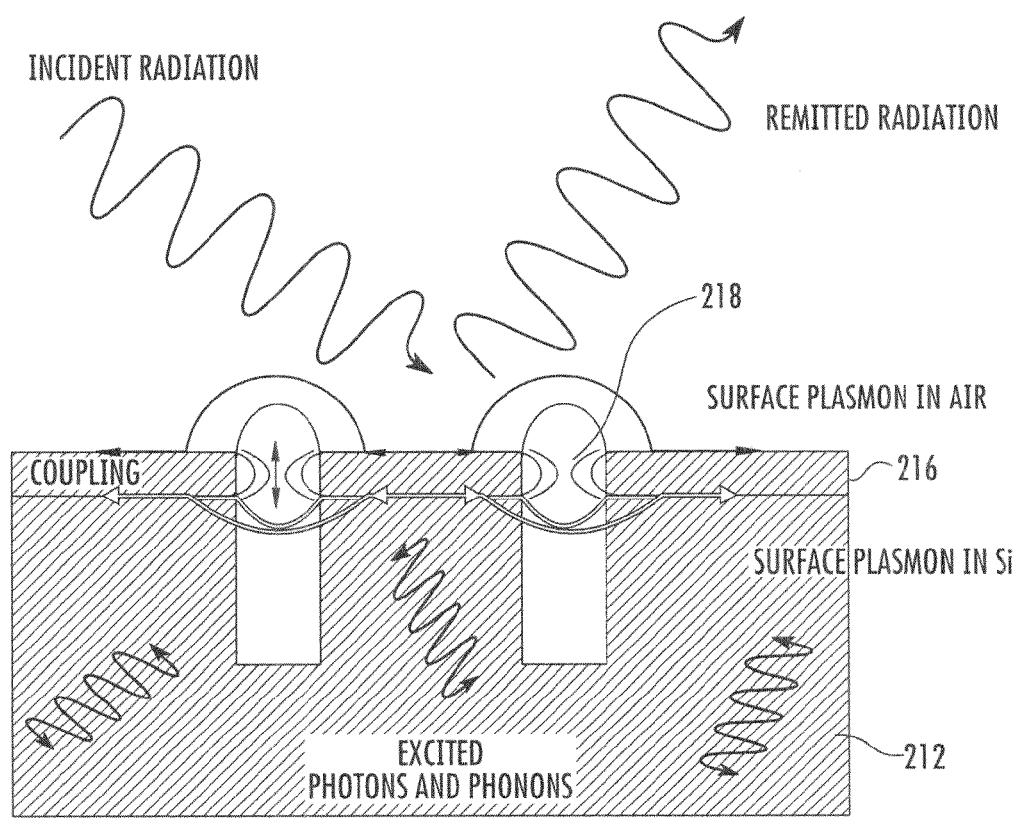
FIG. 6 schematically shows a physical illustration of the emitter device, which employs a photonic crystal structure, according to the present invention.

FIG. 6 schematically shows a physical illustration of the emitter device, which employs a photonic crystal structure, according to the present invention. As shown in FIG. 6, the exemplary emitter device includes a semiconductor material layer 212 and a metallic material layer 216. The semiconductor material layer 212 is thermally excited to emit photons, which are coupled to surface plasmons on the bottom and top surface of the metallic material layer 126, generating strong electromagnetic fields at the edge of the surface features (holes) 218. The spectral characteristics including the location of the central wavelength in a peak, the width of the peak emission, the contrast between the peak and out-peak emissions, the axis of the forward projecting emission (peak emission) of the electromagnetic waves emitted from the emitter device can be modulated by various ways. In particular, emission can be dramatically controlled by small changes in the electromagnetic fields at the edge of the surface features, for example, changing the structure of the edge of the surface features (e.g., sharpness), the size or shape of the surface features, at least partially filling the holes (surface features) with a dielectric material, changing the material of the emitter device, applying a bias voltage or heat to the device, etc. The modulation of the emission will be described in detail below.

Figure 8A:
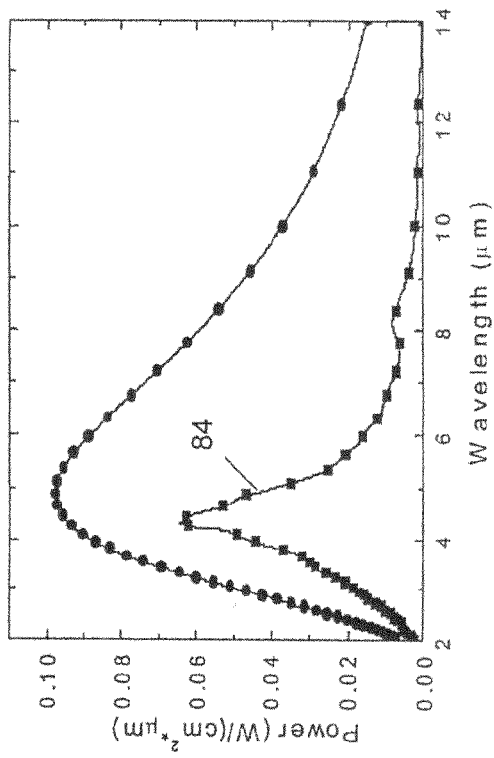
FIG. 8A shows a diagram of spectral characteristics of the emitted electromagnetic energy from the emitter device having the surface features shows in FIG. 7A.
Figure 8B:
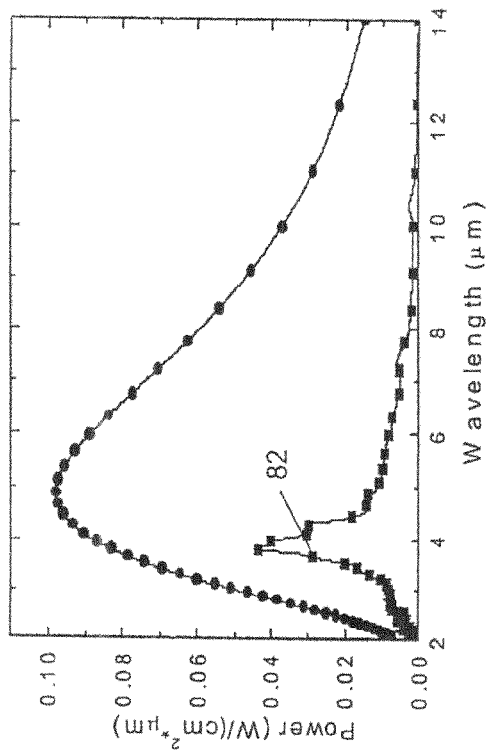
FIG. 8B shows a diagram of spectral characteristics of the emitted electromagnetic energy from the emitter device having the surface features shown in FIG. 7B.
Figure 7A:
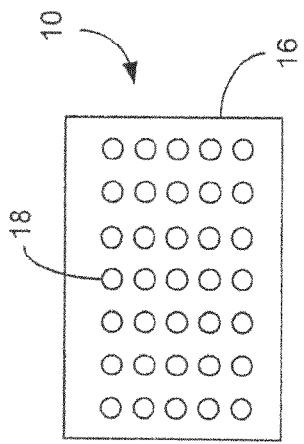
FIG. 7A is a schematic top view of a preferred embodiment of the emitter device according to the present invention, showing a parallelogram distribution geometry of surface features.
Figure 7B:
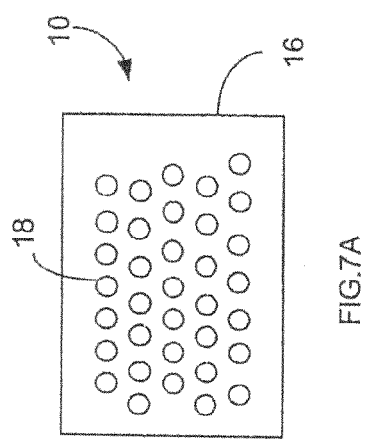
FIG. 7B is a schematic top view of another preferred embodiment of the emitter device according to the present invention, showing a square distribution geometry of periodically distributed surface features.
Figure 7:
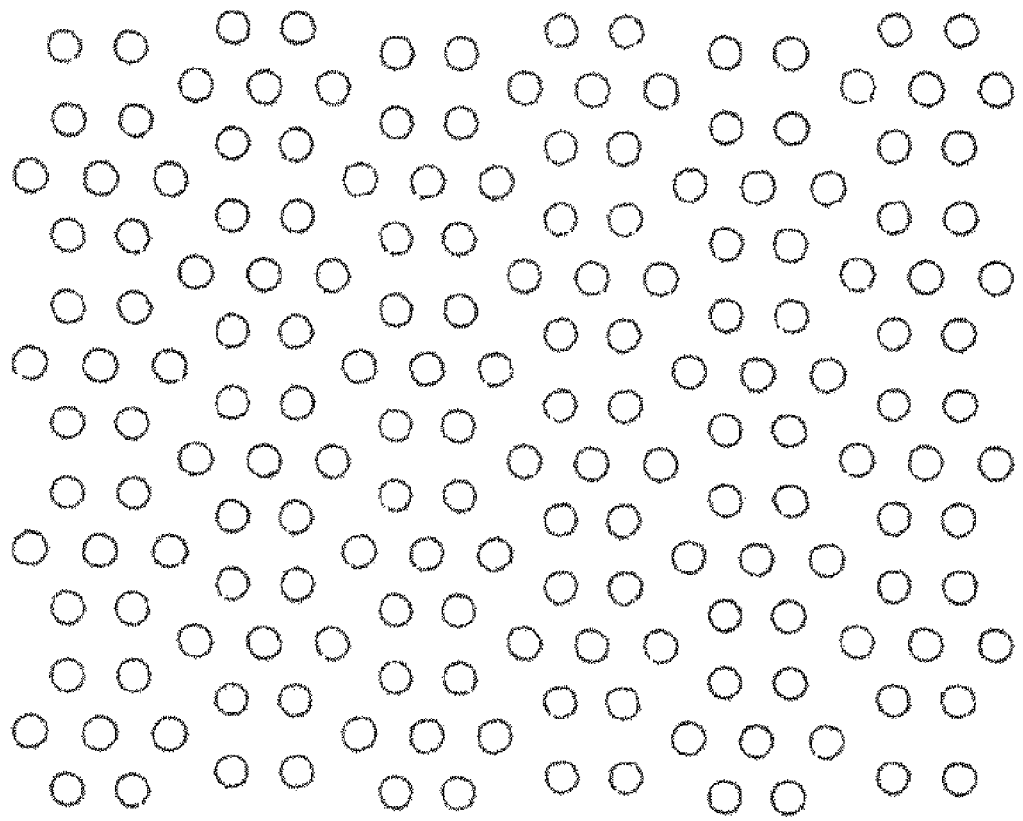
FIG. 7C is a schematic top view of another preferred embodiment of the emitter device of the invention, showing an Archimedean tiling distribution geometry of surface features.

FIG. 7A is a top view of the device 10, which shows a pattern of the holes 18 on the outer surface of the metallic material layer 16. As shown in FIG. 7A, the holes 18 are distributed with a parallelogram geometry having a pair of about 60-degree interior angles (hexagonal geometry). The periodically distributed surface features may be distributed with other patterns, for example, square geometry, as shown in FIG. 7B, or parallelograms in general. Also, quasi-regular geometry can be used, e.g., Archimedean tiling, as illustrated in FIG. 7C. The parallelogram geometry preferably has a pair of 60-degree interior angles, but any other angles can be used. The distribution geometry influences the spectral characteristics of the emission. In other words, the peak emission of the emitter device can be modulated by changing the distribution geometry FIG. 8A shows an emission spectrum (curve 82) corresponding to the hexagonal distribution geometry in FIG. 7A. FIG. 8B shows an emission spectrum (curve 84) corresponding to the square distribution geometry in FIG. 7B. As shown in FIGS. 8A and 8B, the hexagonal geometry (curve 82) has a relatively narrow band peak emission compared to the square geometry (curve 84).

Figure 9A:
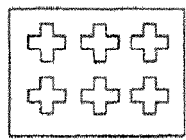
FIG. 9A is a schematic top view of one preferred embodiment of the emitter device according to the present invention, showing a cross shape of the holes etched into the device.
Figure 9B:
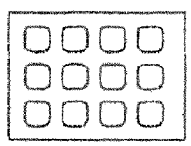
FIG. 9B is a schematic top view of one preferred embodiment of the emitter device according to the present invention, showing a square shape of the holes etched into the device.
Figure 9C:
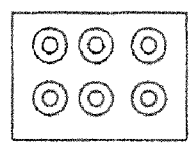
FIG. 9C is a schematic top view of one preferred embodiment of the emitter device according to the present invention, showing a donut shape of the holes etched into the device.
Figure 9D:
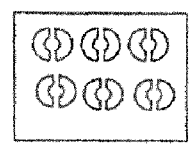
FIG. 9D is a schematic top view of one preferred embodiment of the emitter device according to the present invention, showing a C-reverse-C shape of the holes etched into the device.
Figure 9E:
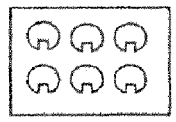
FIG. 9E is a schematic top view of one preferred embodiment of the emitter device according to the present invention, showing a circle-with-a-notch shape of the holes etched into the device.
Figure 9F:
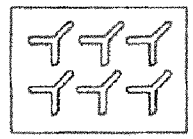
FIG. 9F is a schematic top view of one preferred embodiment of the emitter device according to the present invention, showing a triple-leg shape of the holes etched into the device.
Figure 9G:
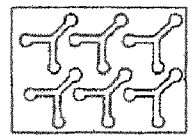
FIG. 9G is a schematic top view of one preferred embodiment of the emitter device according to the present invention, showing a tri-bone shape of the holes etched into the device.

FIGS. 7A and 7B show the holes 18 with a substantially circular shape. The holes 18 can be defined with other shapes, for example, a n-point star shape, such as a cross shape as shown in FIG. 9A or an X shape, a square shape with round-shaped corners as shown in FIG. 9B, a triangular shape, a hexagonal shape, a rectangular shape, a donut (or annular) shape as shown in FIG. 9C, a C-reverse-C shape as shown in FIG. 9D, a circle with a notch shape as shown in FIG. 9E, a triple-leg shape as shown in FIG. 9F, a tri-bone shape as shown in FIG. 9G, or other shapes.

Figure 10:
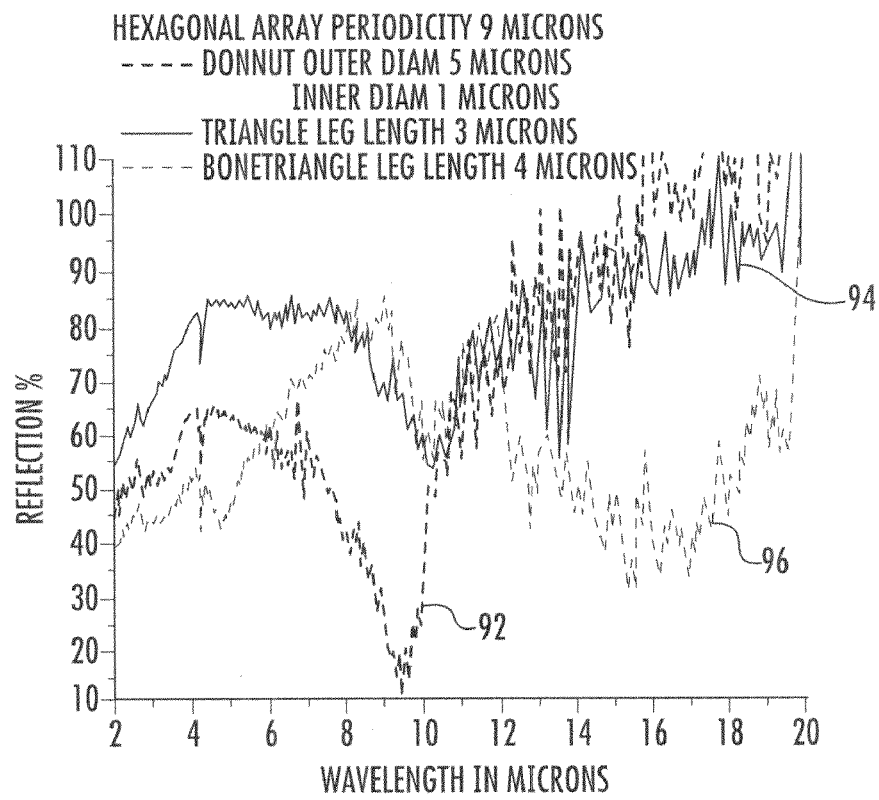
FIG. 10 shows a diagram of spectral characteristics of the emitter devices with holes configured with different shapes.

The shape of the surface features also influences the spectral characteristics of the emission of the emitter device. FIG. 10 shows a diagram of reflection versus wavelength for different shape of holes, all of which employ a hexagonal distribution geometry. The emission or absorption performance of the emitter or absorber device would be the opposite of the reflection performance. In FIG. 10, the curve 92 is a plot of the reflection performance of the emitter device having the donut shape holes as shown in FIG. 9C, the curve 94 is a plot for the triple-leg holes as shown in FIG. 9F, and the curve 96 is a plot for the tri-bone shape holes as shown in FIG. 9G. The spectral characteristics of the peak emission can be tuned by changing the shape of the holes.

Figure 11:
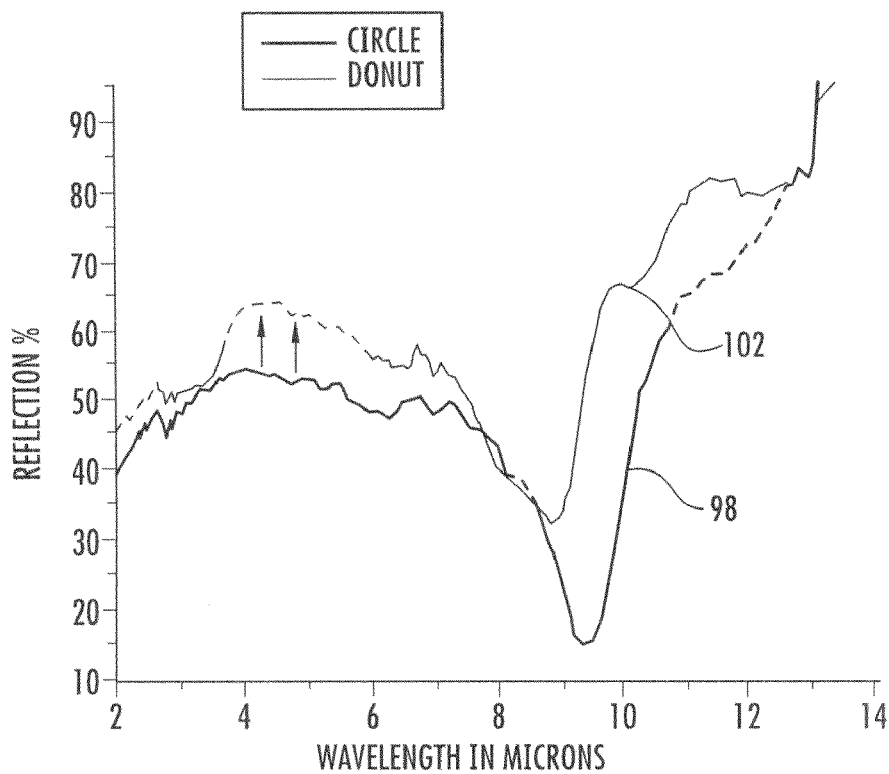
FIG. 11 shows another diagram of spectral characteristics of the emitter devices with holes configured with different shapes.

For another example, a diagram of reflection versus wavelength performance curves for circular holes and donut holes are shown in FIG. 11. As seen in FIG. 11, the short wavelength reflection of the emitter device with the donut shape holes is improved (the curve indicated by reference number 98) compared to the emitter device with the circular holes (the curve indicated by reference number 102), which means the contrast between the peak emission and the shot wavelength emission is improved in the emitter device with donut shape holes. As shown in FIG. 11 the shape of the surface features also influences the location of the wavelength of resonance (the peak wavelength). The device with the donut holes has a longer peak wavelength (curve 98), and the device with the circular holes has a shorter peak wavelength (curve 102).

Figure 12:
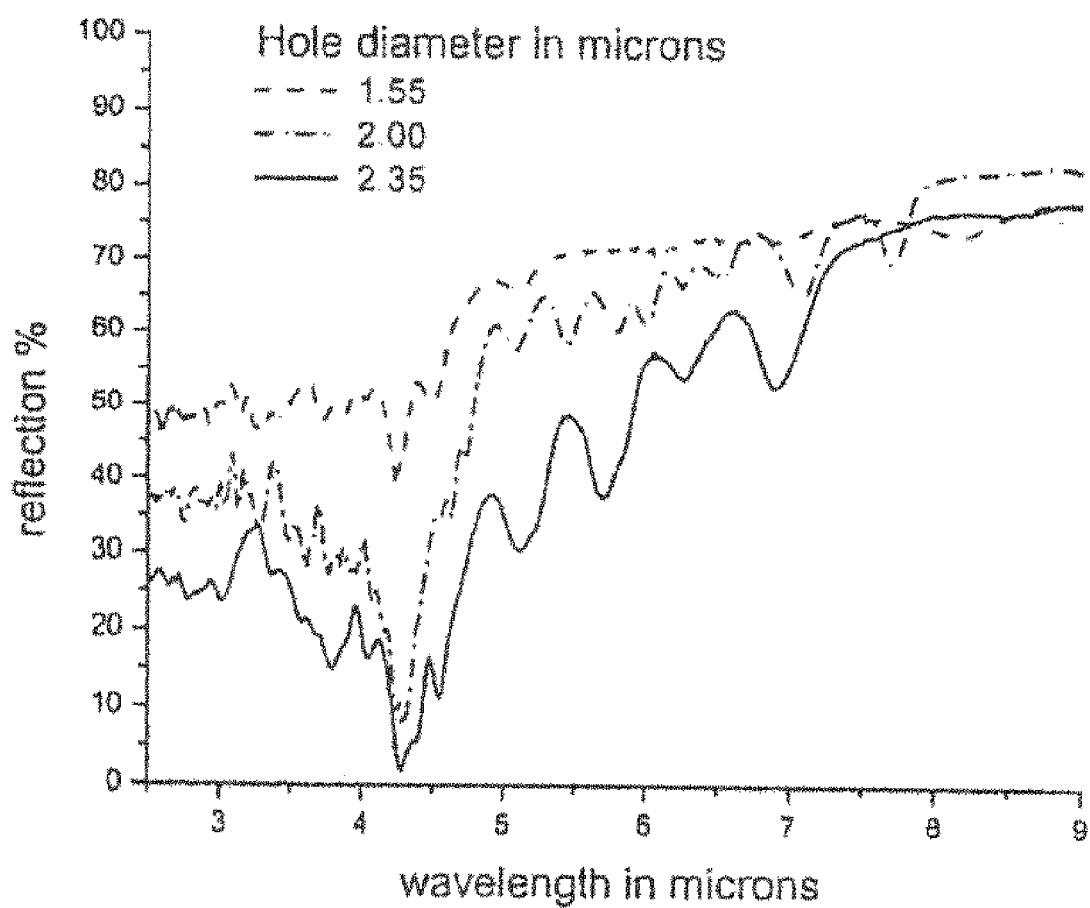
FIG. 12 shows a diagram of spectral characteristics of the emitter devices with holes configured with different diameters.

The diameter of the holes 18 can be varied in different embodiments. The diameter of the holes has an effect on the spectral characteristics of the emission. FIG. 12 plots reflection versus wavelength for the emitter devices with different hole sizes. Other parameters other than the hole size of the emitter devices compared in FIG. 12 such as the distribution geometry of the holes are the same. In general, small holes give small contrast in signal and weak resonance, medium size holes give good signal contrast and narrow bandwidth and larger holes give good signal contrast and because they have enhanced strength in the side resonances they also have broader bandwidth, and consequently an overall large signal. In the diagram in FIG. 12, the curve 122, which corresponds to holes with a diameter of 2.45 μm, has a relatively smaller width of peak emission (low reflection in FIG. 12), and the curve 124, which corresponds to relatively small holes with a diameter of 1.55 μm, has a larger width of peak emission. The curve 122 also shows an improved contrast between the peak emission and the out-peak emission.

Figure 13A:
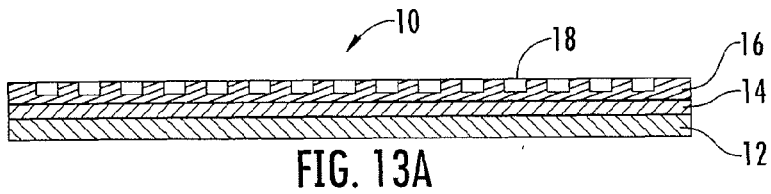
FIGS. 13A-13F schematically show cross-sectional views of the emitter devices having holes configured with different depth.
Figure 13B:
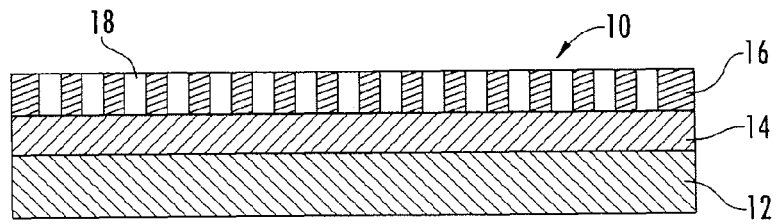
Figure 13C:
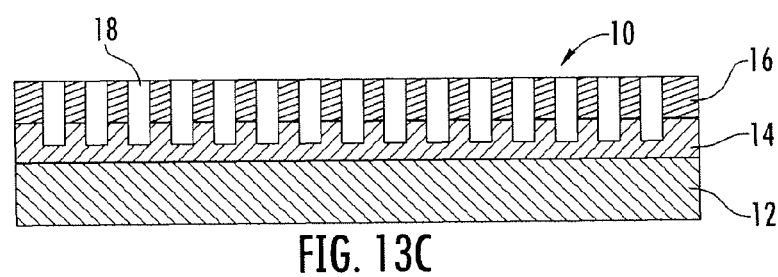
Figure 13D:
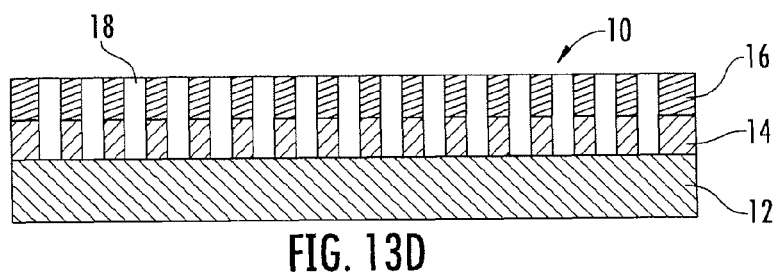
Figure 13E:
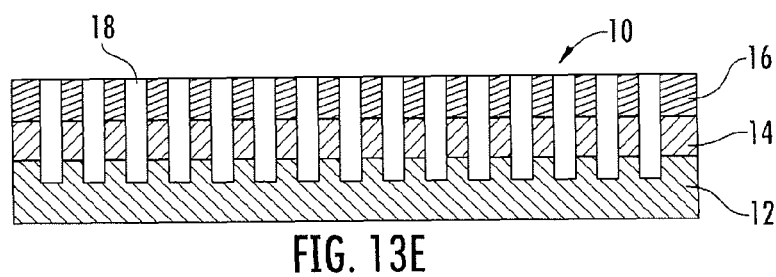
Figure 13F:
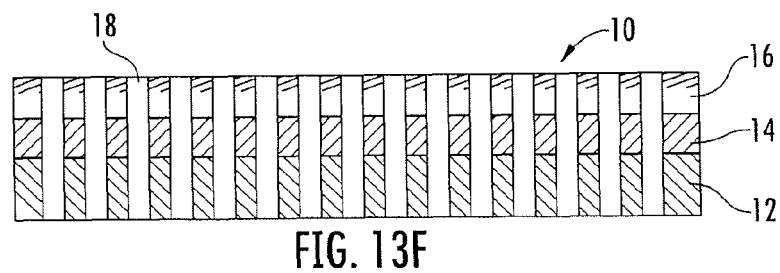

The holes 18 can be defined with different depths in different embodiments. For example, the holes 18 may extend partially into the metal layer 16 as shown in FIG. 13A, or extend through the metal layer 16 as shown in FIG. 13B, or extend through the metal layer 16 and into a portion of the dielectric layer 14 as shown in FIG. 13C, or extend through the metal layer 16 and the dielectric layer 14 as shown in FIG. 13D, or extend through the metal layer 16 and the dielectric layer 14, and into a portion of the semiconductor layer 12 as shown in FIG. 13E, or extend through the metal layer 16, the dielectric layer 14, and the semiconductor layer 12 as shown in FIG. 13F.

Figure 14:
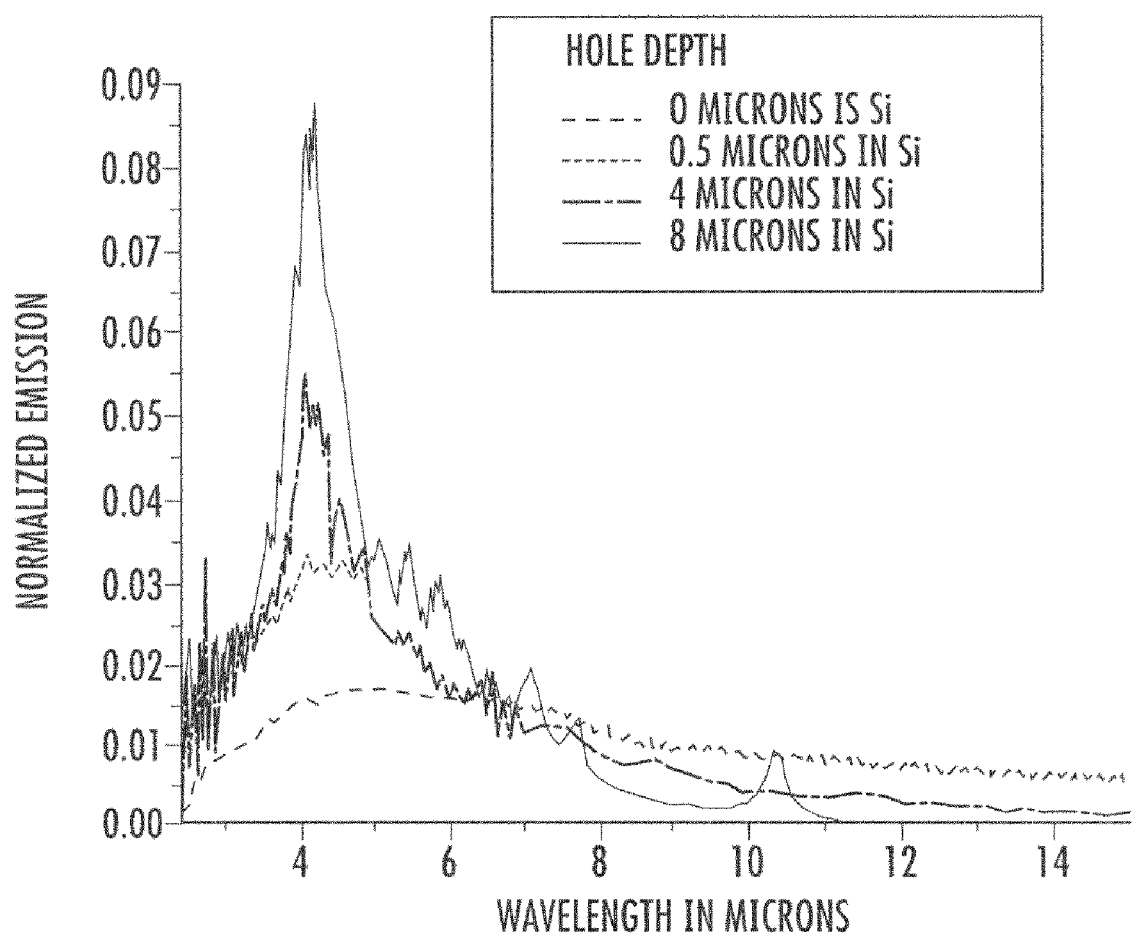
FIG. 14 shows a diagram of spectral characteristics of the emitter devices with holes configured with different depth.

FIG. 14 illustrates a diagram which shows the effects of the depth of holes on the spectral characteristics of the emission. The emitter devices studied in FIG. 14 employ a metal-on-silicon structure as shown in FIG. 3. As shown in FIG. 14, the emitter with deeper holes has a narrower and higher peak emission (curve 146, holes etched through the metal layer and 8 μm into the silicon), compared to the emitters having shallow holes as plotted by the curve 142 (4 μm into the silicon), curve 144 (0.5 μm into the silicon), and curve 148 (holes etched only in the metal layer). FIG. 14 shows that the spectral characteristics of the emission can be modulated by changing the depth of the holes.

Figure 15A:
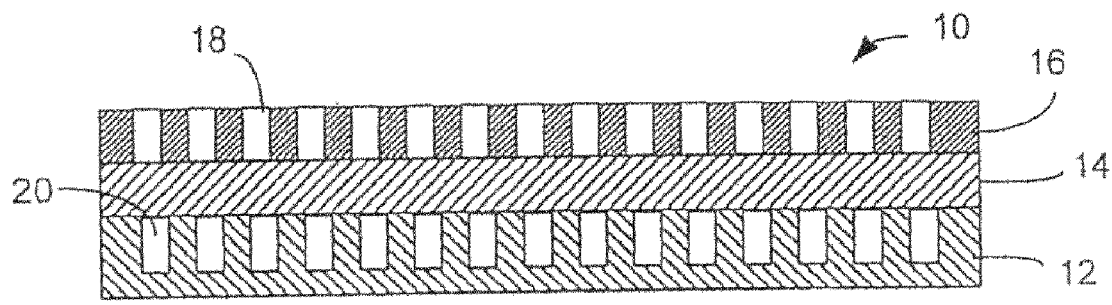
FIG. 15-15C are schematic cross-sectional views of preferred embodiments of the emitter device according to the present invention.
Figure 15B:
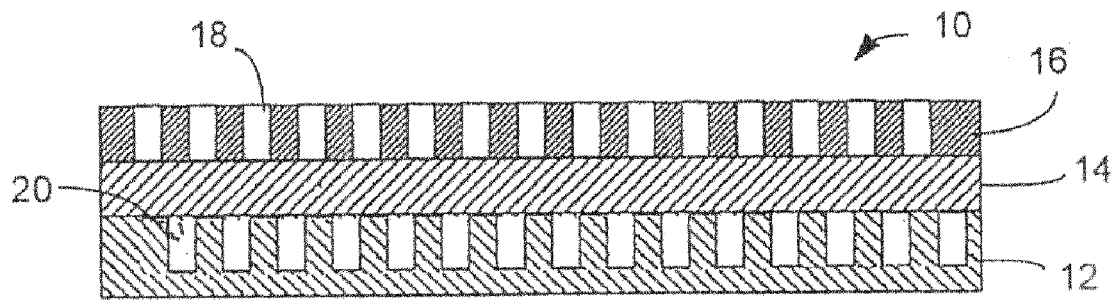
Figure 15C:
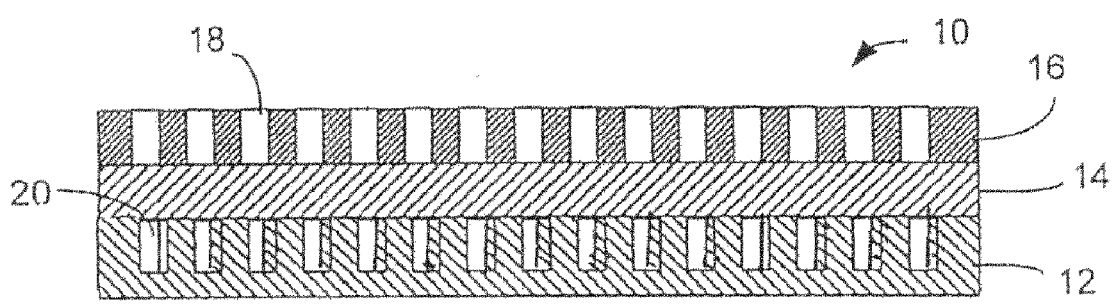

FIG. 15A-15C illustrate a further embodiments, in which the holes 18 extend through the metal layer 16 and the semiconductor material layer 12 defines an array of periodically distributed holes 20 individually extending through at least a portion of the semiconductor material layer 12. In the embodiment of FIG. 15A, the holes 18 of the metal layer 16 and the holes 20 of the semiconductor layer 12 have the same geometry and are axially aligned. In the embodiment of FIG. 15B, the holes 18 and 20 have the same geometry but are not axially aligned. In the embodiment of FIG. 15C, the holes 18 and 20 have different geometry and are not axially aligned.

Figure 16A:
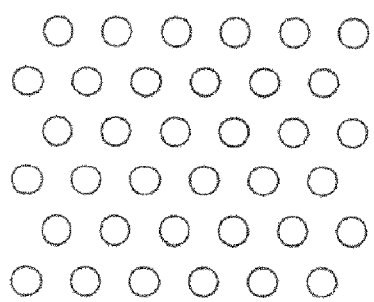
FIGS. 16A and 16B schematically show top views the emitter devices having holes configured with different periodicities.
Figure 16B:
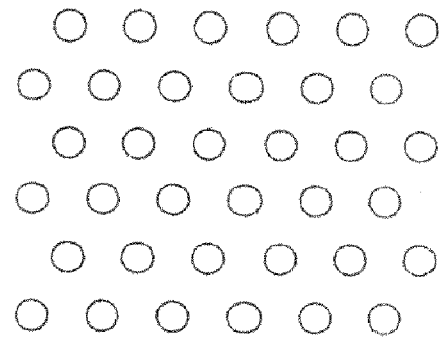
Figure 17:
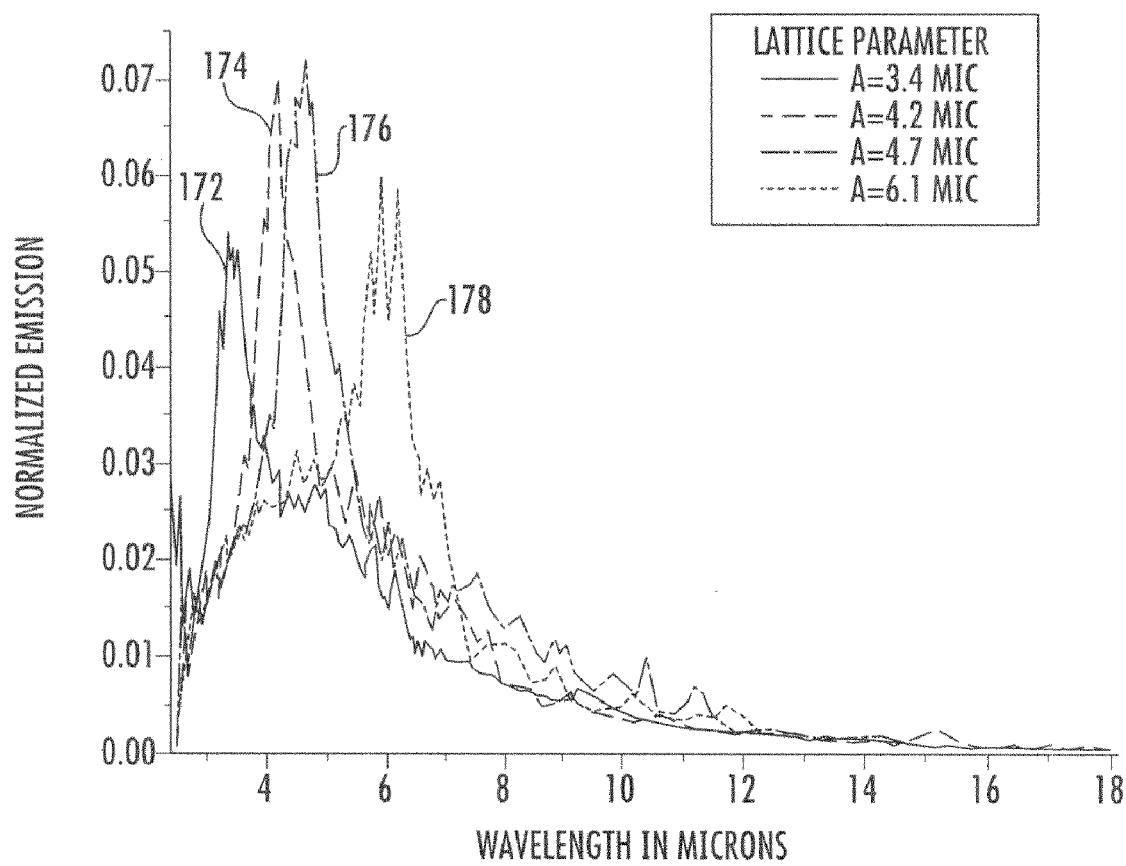
FIG. 17 schematically shows a diagram of spectral characteristics of the emitter devices with holes configured with different periodicities.

According to one aspect of the present invention, the location of the peak wavelength is related to the periodicity (center-to-center spacing between two holes) of the holes. In particular, the peak wavelength is substantially linearly proportional to the periodicity of the holes. FIG. 16A shows a top view of an emitter device having a relatively small center-to-center spacing between the holes and FIG. 16B shows a top view of an emitter device having a relatively large center-to-center spacing between the holes. FIG. 17 illustrates a diagram which shows the effects of the periodicity of the holes on the spectral characteristics of the emission. As shown in FIG. 17 the emitter device with the regular array of holes having a relatively smaller periodicity (the curve 172) produces a shorter peak wavelength and larger periodicities produce longer peak wavelengths (the curves 174, 176, and 178). FIG. 17 shows that the location of the peak wavelength of the emission can be modulated by changing the periodicity of the surface features.

Figure 18A:
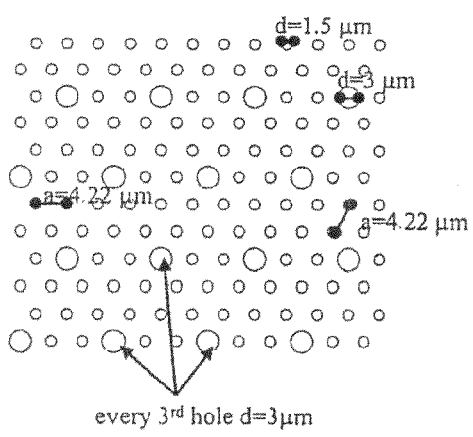
FIGS. 18A and 18B schematically show top views the emitter devices having defects.
Figure 18B:
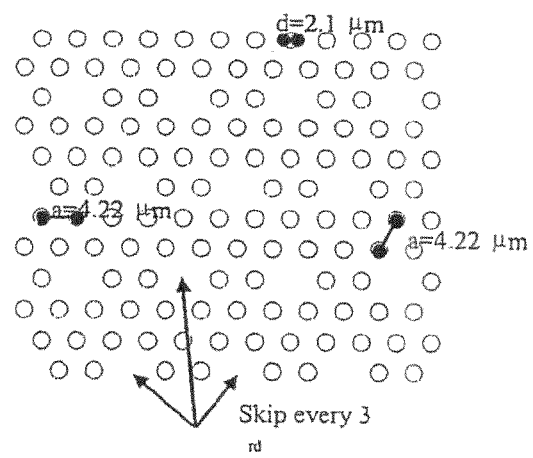

According to another aspect of the present invention, the emitter device includes a regular array (periodically distributed) of "defects". Defects are elements or features that have structural differentiae that do not belong to the periodically distributed surface features. In other words, the defects include a characteristic trait distinguishing the defects from the periodically distributed surface features. FIG. 18A illustrates one exemplary embodiment, in which the periodically distributed surface features includes an array of circular holes each having a diameter D1=1.5 µm distributed in a hexagonal geometry with a periodicity of 4.22 µm, and the regular array of defects include larger holes each having a diameter D2=3 µm occurred at the position of every third hole of the periodically distributed surface features. FIG. 18B illustrates another exemplary embodiment of the present invention, in which the regular array of defects are implemented by deliberately missing every third hole in the hexagonal array of holes. The defects can be implemented by employing any structural differentia that is different from the periodically distributed surface features. For example, if the periodically distributed surface features are holes, the defects can be holes with different size, shape, or depth. In one form, the periodically distributed surface features include circular holes, and the defects are circle-with-notch-shaped (as shown in FIG. 9E) holes. The defects also can be holes filled with other materials such as a dielectric material or a non-linear optical material. It is not necessary that the defects occur at the position of every third surface feature. The defects may be implemented with other distribution geometries or periodicities, for example, occurring at the position of every fourth surface feature.

Figure 19:
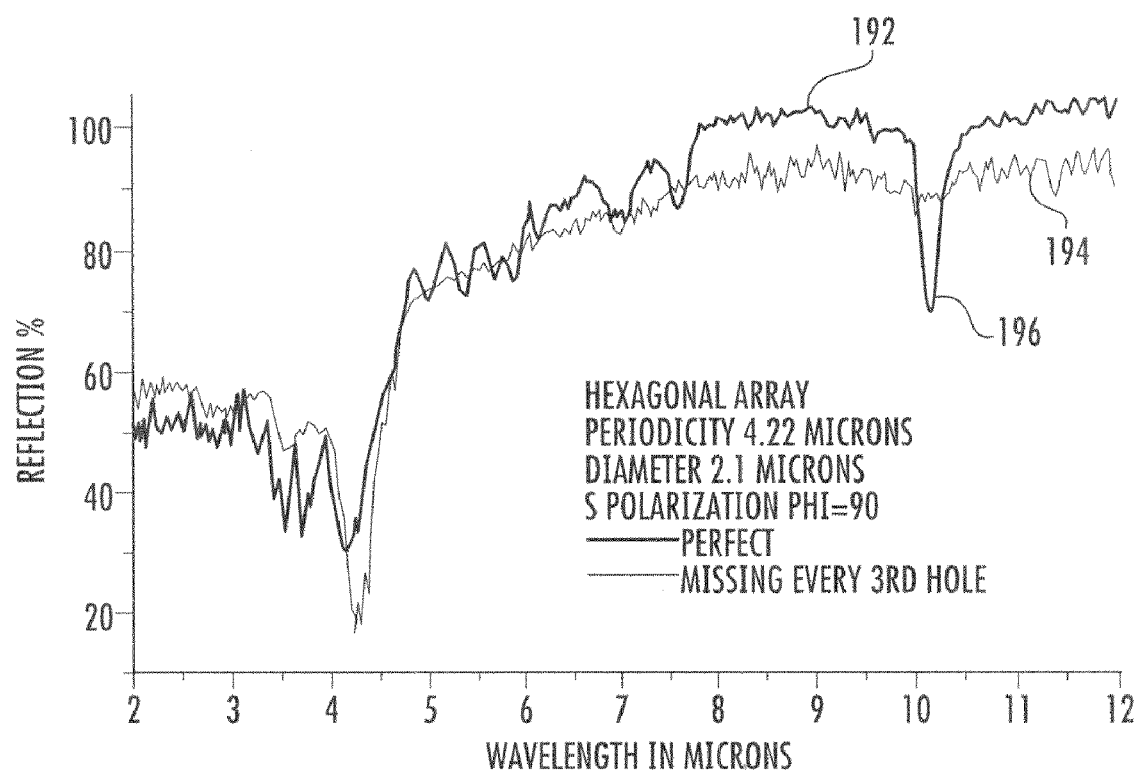
FIG. 19 schematically shows a diagram of spectral characteristics of the emitter device having defects compared with the emitter device without defects.

FIG. 19 illustrates a diagram of reflection versus wavelength performance curves for comparison between a regular array of surface features (without defects) (reference number 192) and a regular array of surface features together with a regular array of defects (reference number 194). As shown in the diagram, the curve 192 has a secondary resonance as indicated by reference number 196. However, on the curve 194, the secondary resonance is relatively smooth compared to the curve 192 because some of the higher order (side) resonances are quenched. FIG. 19 shows that the emission spectrum of an emitter device with the regular array of defects shows a strong peak emission and a smooth out-peak emission. The emitter device having the periodically distributed surface features without the regular array of defects emits light with a spectrum having a primary resonance together with multiple secondary resonances, and thereby the contrast between the peak emission and the out-peak emission is not as strong as the emitter devices with periodically distributed surface features together with the regular array of defects.

Figure 20:
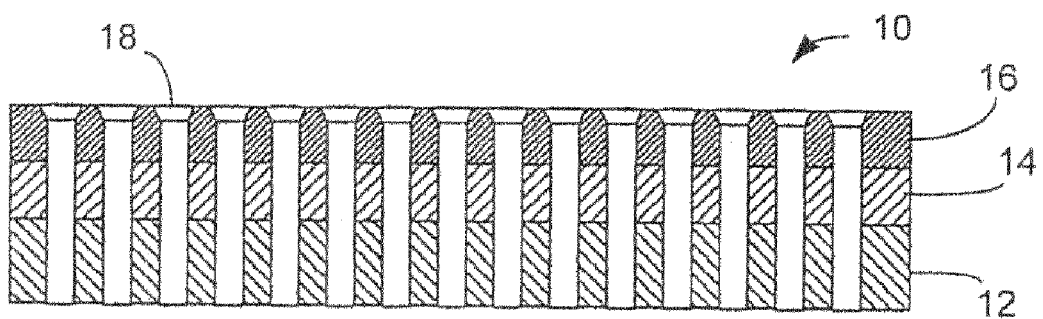
FIG. 20 is a schematic cross-sectional view of a preferred embodiment of the emitter device according to the present invention.

The spectral characteristics of the emitted/absorbed electromagnetic energy can also be tuned by selecting the materials of the layers of the device, thickness of the layers, dopant type and concentration in the materials, or by changing other material properties of the emitter device such as changing the geometry of the edge of the holes as shown in FIG. 20 (the holes having a triangular edge), changing the index of refraction of the materials, changing the conductivity of the materials, etc.

Figure 21:
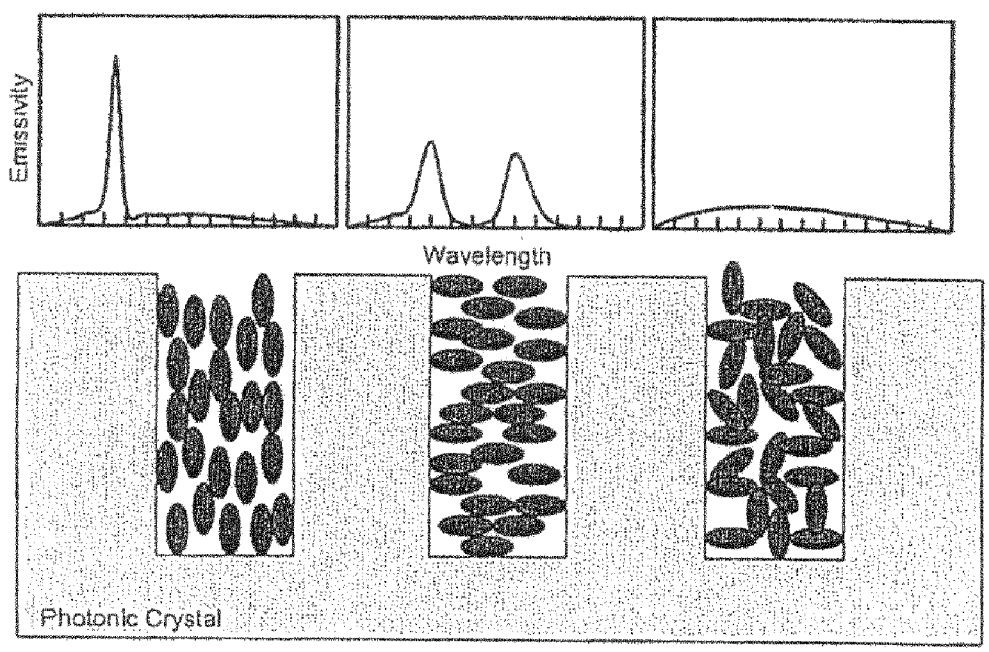
FIG. 21 schematic shows an emitter device having holes filled with materials together with schematic diagrams representative of spectral characteristics corresponding to the orientation of the filled materials.

According to another aspect of the present invention, the spectral characteristics of the emission can be modulated by at least partially filling the holes with different materials, or by changing the property of the filling materials, for example, doping, applying an voltage to the filling materials, etc. In one preferred form, the holes of the emitter device are filled with a material preferably selected from, but not limited to, a dielectric material, a non-linear optical material, a liquid crystal material, a piezoelectric material, a pyroelectric material, a ferroelectric material. The optical and/or electronic properties (e.g., permittivity, conductivity, polarization) of those materials can be actively controlled, for example, by applying or changing a bias voltage, changing the temperature, etc., thereby to modulate the spectral characteristics of the emission. FIG. 21 shows schematic diagrams representative of emissivity versus wavelength corresponding to the orientation of the filling materials. As shown in FIG. 21, in a first regular state, a narrow band of emission can be achieved. In a second regular state, two bands of peak emission can be achieved. In an irregular state, the peak emission is almost not recognizable. In one preferred form, the holes filled with a filling material as described above may be individually addressable. According to another aspect of the present invention, if the device having holes filled with a dielectric material, the spectral characteristics of the emission can be modulated by changing the permittivity or the index of refraction of the dielectric material or by doping dielectric material. In another preferred form, in the embodiment having donut shape holes, the permittivity or other properties of the central pillars can be changed to modulate the emission. In yet another form, diode antenna posts are deposited on the dielectric layer or semiconductor layer. The properties of the diode antenna posts can be actively controlled, for example, by bias voltage, thereby to modulate the emission.

Figure 22:
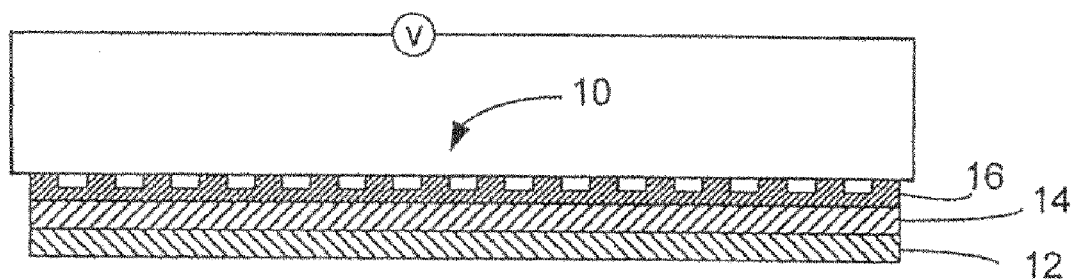
FIG. 22 is a schematic cross-sectional view of a preferred embodiment of the emitter device according to the present invention.

According to another preferred embodiment of the present invention, the spectral characteristics of the emitted absorbed electromagnetic energy can be actively modulated when the device is in use by applying (or changing) a bias voltage to the device or inducing (or changing) charges to the device. In one preferred form, the metallic layer of the emitter device is biased with a voltage as shown in FIG. 22. Changing the bias voltage modulates the spectral characteristics of the emission. In one preferred embodiment, the metallic material layer can use indium tin oxide (ITO), which can be deposited on the dielectric or semiconductor layer by electron beam evaporation or sputtering. The optical and electronic properties of ITO films are dependent on factors such as deposition parameters, density of charge carriers, bias voltage, etc.

Figure 23:
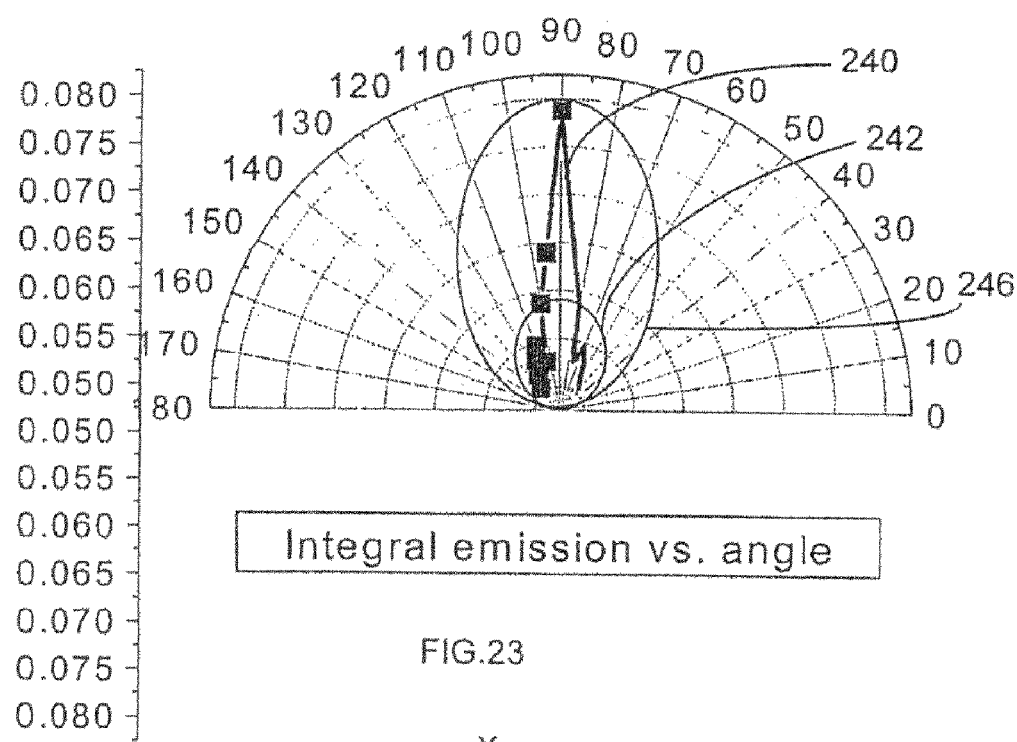
FIG. 23 schematically shows a diagram of spectral characteristics of the emitted electromagnetic energy from the emitter device.
Figure 24A:
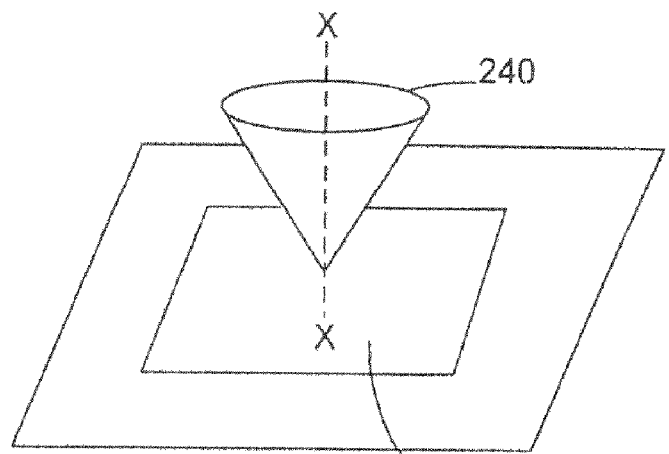
FIGS. 24A and 24B schematically show the emitter devices together with the emitted electromagnetic energy.
Figure 24B:
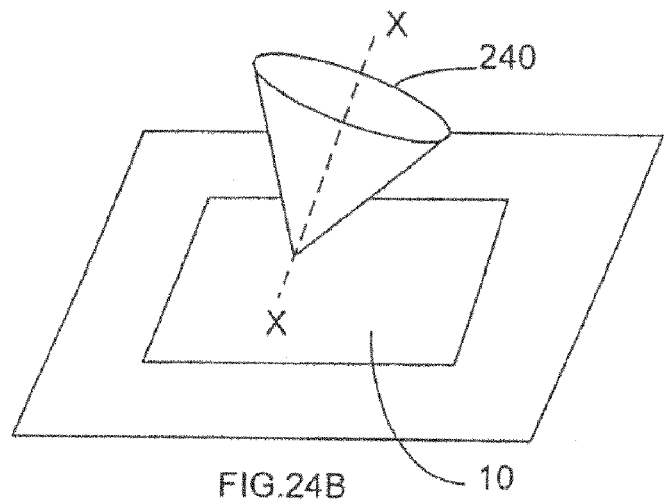

The peak emission (in-band emission) of the emitted infrared light from the emitter device according to the present invention forward projects in a narrow angular or conical range (e.g., a cone) extending about a central axis X as indicated by reference number 240 in FIG. 23 and FIGS. 24A and 24B. The out-peak emission (out-band emission) looks like emission from a grey body source with a low broadband emissivity, as indicated by reference number 242. The circle 246 indicates total radiation, such as radiation from a blackbody. As seen in FIG. 23, the in-band emission is in a narrow angular range, while the out-band and the total emission have a relatively wide projecting angle.

Typically, the central axis X of the forward projecting light is perpendicular to the principal plane of the emitter device 10 as shown in FIG. 24A. The central axis X of the forward projecting light (peak emission) can be offset with respect to the axis perpendicular to the principal plane as shown in FIG. 24B by adjusting the parameters of the surface features. For example, in the embodiment in which the surface features employ a circle with a notch shape as shown in FIG. 9E, the axis of the forward projecting light emitted from the emitter device is oblique with respect to the principal plane of the device.

Figure 25A:
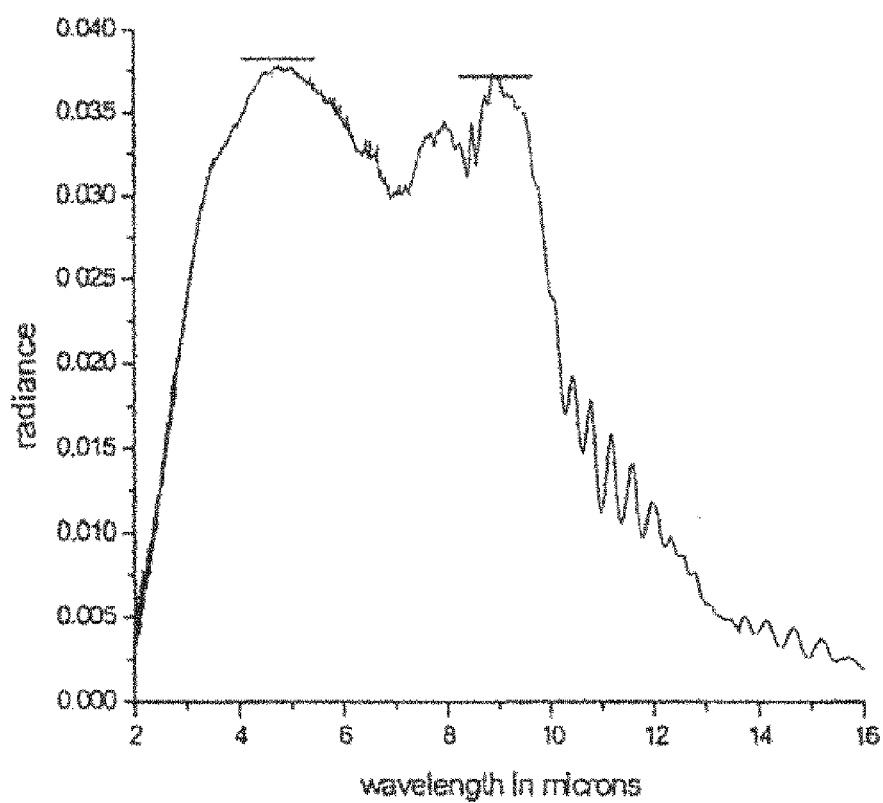
FIGS. 25A and 25B schematically show diagrams of spectral characteristics of the emitter devices according to one aspect of the present invention.
Figure 25B:
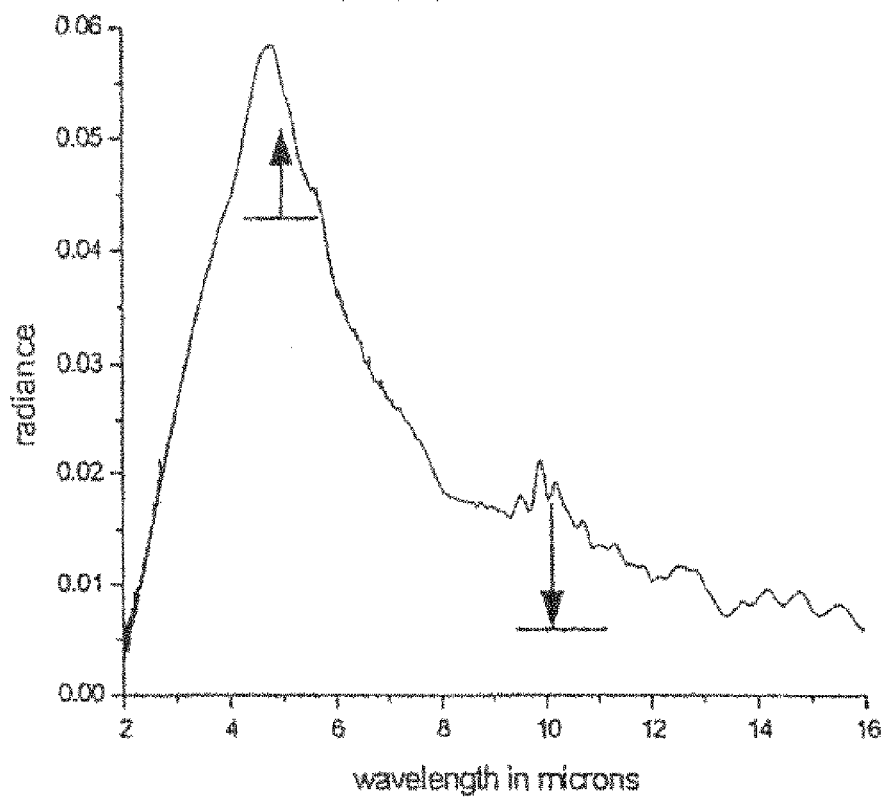

By adjusting the shape, dimension, and periodicity of the surface features, two bands of enhanced radiation instead of just one can be achieved as shown in FIG. 25A. By further changing the dimension or other parameters of the surface features, the two bands of enhanced radiation can be selectively turned on and off as shown in FIG. 25B.

Figure 26A:
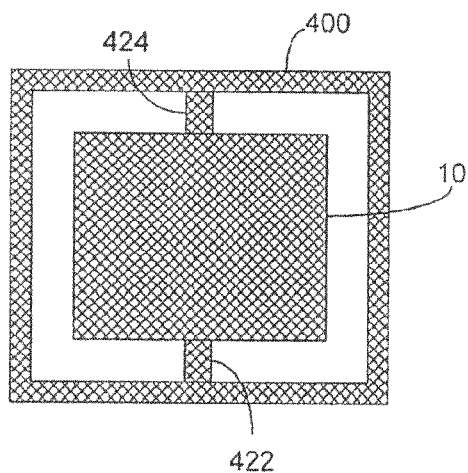
FIGS. 26A-26D schematically show top views of the emitter devices according to the present invention, showing the emitter devices in a form of a membrane suspended in a frame.
Figure 26B:
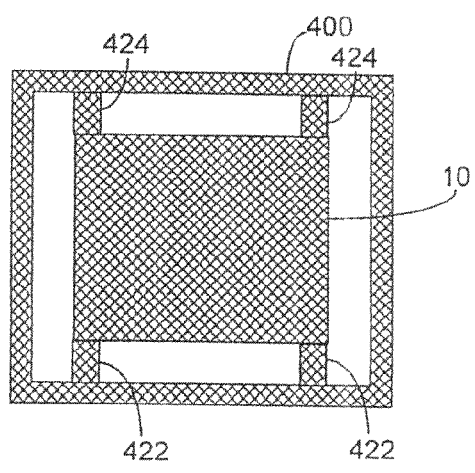
Figure 26C:
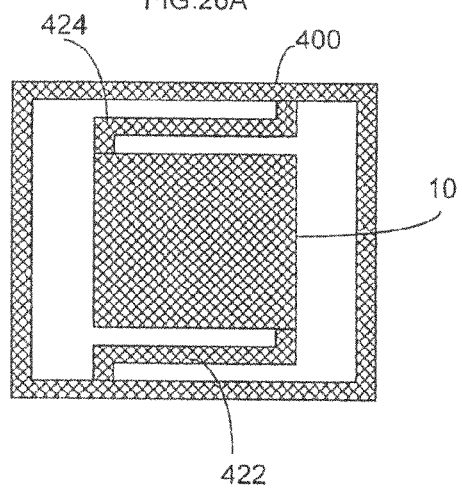
Figure 26D:
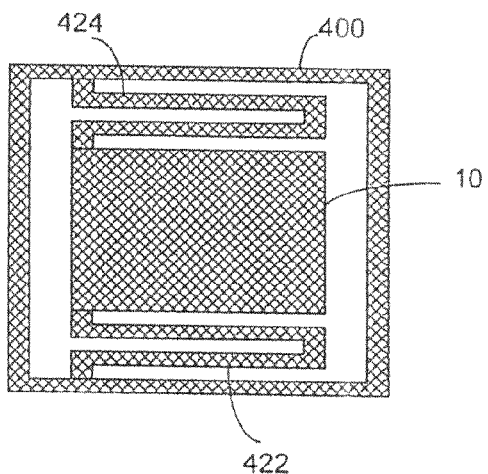

According to a further aspect of the present invention, the emitter devices described above are preferably configured with a shape of a membrane. Preferably, but not necessarily, the membrane has an aspect ratio of the length or width to the thickness greater than 10. As shown in FIG. 26A, the membrane 10, 100, or 200 (hereinafter only the device 10 is used as an exemplary embodiment) is suspended from a frame 400 by two uniaxial suspension arms 422 and 424. The resulting device is a MEMS device. The frame 400 and the suspension arms 422, 424 can be made from silicon, silicon carbide, or other materials. Preferably the membrane 10, suspension aims 422, 424, and the frame 400 are made from one semiconductor wafer and are constructed as an integral structure. The suspension arms 422 and 424 can be electrically conductive thereby to conduct electrical energy to the semiconductor layer 12 of the device 10 to heat the semiconductor layer 12. Preferably the membrane 10 is thermally isolated from the frame to increase the accuracy of the device. The resulting MEMS device can be configured with other structures. For example, the suspension arms may employ other shapes such as "H", "S", and "U" shape as shown in FIGS. 26B, 26C, and 26D. For another example, the membrane 10 may be supported by supporting legs 426 and 428 on a substrate 402, as shown in FIG. 27B. (Although only two legs are shown in the figure, the MEMS device may include more than two legs). Contacts can be formed on the supporting legs 426 and 428 for conducting electrical energy to the semiconductor layer 12 of the device 10.

The fabrication of the devices may utilize MEMS manufacturing methods available in the art, which generally includes a number of photolithography and etching steps. Fabrication of the structure of the device 10 as shown in FIG. 2, which uses a relative thick silicon layer as the semiconductor layer 12 may include growing oxide on a silicon substrate to form the silicon dioxide layer 14, depositing a metal layer 16 on the silicon dioxide layer 14, applying photoresist on the metal layer 16 and patterning the photoresist, and etching the structure to form the holes 18 on the device 10. As described above, the periodically distributed surface features may employ different configurations in different embodiments, and therefore, different masks may be used to achieve these different patterns of the periodically distributed surface features.

In another preferred embodiment, the two-dimensional PC patterns are processed in a passivated Si substrate. The PC pattern was photolithographically defined, followed by reactive ion etching (RIE) through the passivation layer and into the Si substrate. A second photolithographic step can be used to mask-off the etched holes, followed by e-beam evaporation of Ti, Pt, and Au. A liftoff process employing organic solvents is used to remove photoresist and excess metal.

Fabrication of the structures of the devices 100 and 200 as shown in FIGS. 3 and 4 are similar to the fabrication process of the device 10 in FIG. 2 as described above. For example the device 100 shown in FIG. 3 can be manufactured using the similar steps described above by skipping the growing oxide step.

In the embodiments in which silicon carbide is used as the semiconductor layer, an example process used to fabricate the devices is the Multi-User Silicon Carbide (MUSiC) process. The MUSiC process is available in the art, (see J. M. Melzak, A. Leppart, S. Rajgopal, and K. M. Moses, "MUSiC—An Enabling Microfabrication Process for MEMS," Commercialization of Micro Systems Conference (COMS 2002), Ypsilanti, M I, Sep. 8-12, 2002). Silicon carbide devices are disclosed in U.S. patent application Ser. No. 11/156,081, filed Jun. 17, 2005.

Fabrication of the structures on thin membranes as shown in FIGS. 26A-26D, 27A, and 27B may utilize a sacrificial layer to support the membrane and after the structures of the membrane and the suspension anus are defined and the periodic features are formed on the top surface of the device, the sacrificial layer is removed using an etchant with high selectivity of the material of the sacrificial, layer over the materials of the device.

Figure 27A:
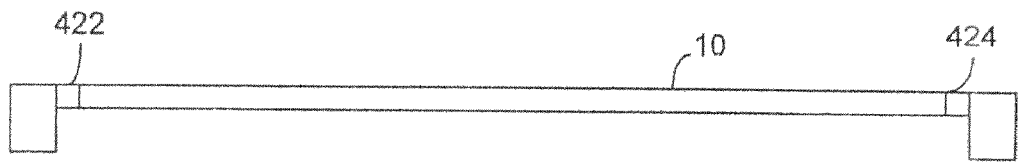
FIG. 27A is a schematic side view of one preferred embodiment of the emitter device according to the present invention, showing a membrane suspended on a substrate.
Figure 27B:
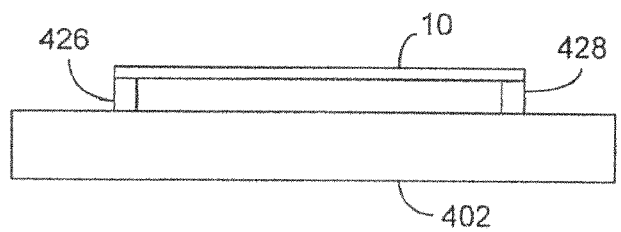
FIG. 27B is a schematic side view of another preferred embodiment of the emitter device according to the present invention, showing a membrane supported on a substrate.

In one preferred form, the MEMS device as depicted in FIGS. 26A-26D, 27A and 27B is fabricated on an SOI silicon wafer, which includes a device layer, a dielectric layer, and a handle layer. The PC etch is performed to pattern the membrane. Then the membrane is defined in the device layer using deep reactive ion etching (DRIE). The device is released by a backside-through etch, resulting in a suspended membrane structure spanning an open cavity, as shown in FIG. 27A. A sacrificial material may be deposited to support the membrane. The sacrificial material is then removed from the device.

While the above embodiments exemplify methods for forming the emitter devices, any other manufacturing process suitable for forming the structures may be used. For example, the emitter may be formed on a separate membrane and then is bonded to a frame or substrate using wafer bonding techniques.

Figure 28A:
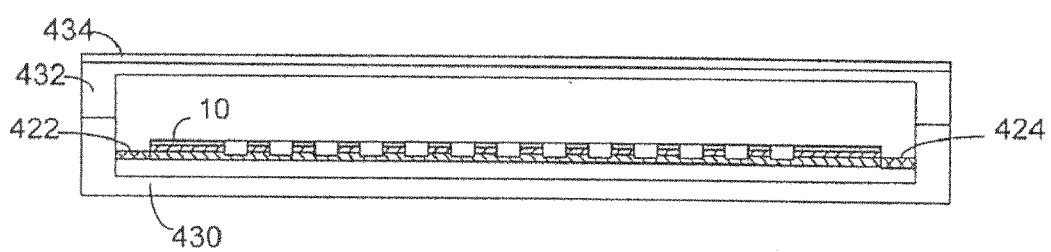
FIG. 28A is a schematic cross-sectional view of one preferred embodiment of the emitter device according to the present invention, showing a device packaged in an enclosure.
Figure 28B:
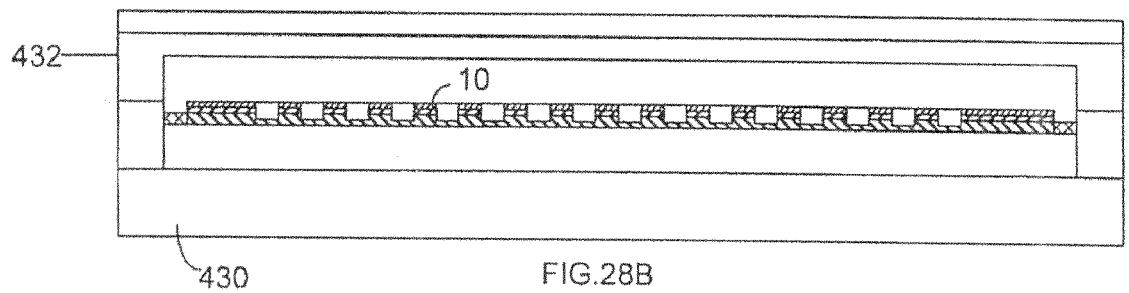
FIG. 28B is a schematic cross-sectional view of one preferred embodiment of the emitter device according to the present invention, showing a device packaged in an enclosure.

FIG. 28A illustrates a further preferred embodiment, in which the emitter/detector device 10 is suspended by suspension arms 422 and 424 from a substrate or frame 430. The device 10 is covered by a transparent covering 432 which is preferably coated with a thin film 434 to decrease reflection of the transparent covering 432. In one preferred form, the transparent covering 432 is made from silicon. The thickness of the transparent covering 432 and the thin film 434 are arranged to achieve optimal transmission of a particular light spectrum that the emitter/detector is designed to emit/detect. The covering 432 is bonded to the substrate 430 and the emitter/detector device 10 is sealed in the interior region formed by the substrate 430 and the covering 432 from the outside environment. The interior region formed by the substrate 430 and the covering 432 is preferably vacuum) although the interior region can be maintained at atmosphere pressure or other pressures as desired. FIG. 28B shows a three wafer structure, in which the device 10 is fabricated on one wafer as shown in FIG. 27A, and is sandwiched between a substrate wafer 430 and a covering wafer 432.

A person skilled in the art should understand that the processes described above and in the figures only briefly illustrate the fabrication processes, and some detailed steps are not described in the description and in the figures. One skilled in the art should appreciate the whole fabrication process from the exemplary embodiments illustrated in the present disclosure. The specification describes the steps of the preferred processes in a sequence, but a person skilled in the art should understand that it may not be necessary to perform these steps in the sequence as described.

The present disclosure has described the devices and methods of producing the devices in a single device level. Such devices are typically fabricated in large numbers on a wafer of a semiconductor material. The wafer scale assembly is then separated into individual devices. A person skilled in the art should appreciate that the wafer scale fabrication uses the same process as described above.

In wafer level manufacturing and packaging, an array of the emitter devices (which can be any embodiment as described above) are first fabricated on a wafer. Another wafer is etched to form an array of transparent coverings. The two wafers are then aligned and are bonded together. It is preferred that the two wafers are bonded together by silicon direct bonding. Silicon direct bonding which is also called silicon fusion bonding, is a wafer-to-wafer bonding technology known in the art. Other alternatives wafer bonding techniques also can be used, which include but are not limited to anodic bonding, intermediate-layer bonding, glass frit bonding and the like. The two bonded wafers with the sealed emitter devices disposed inside are then separated into individual devices. In the example where the membrane is released using a backside through wafer etch a third wafer is bonded to the backside of the device wafer sealing the backside of the device. Then the transparent covering wafer is bonded to the two wafer stack completing the sealed package.

Figure 29:
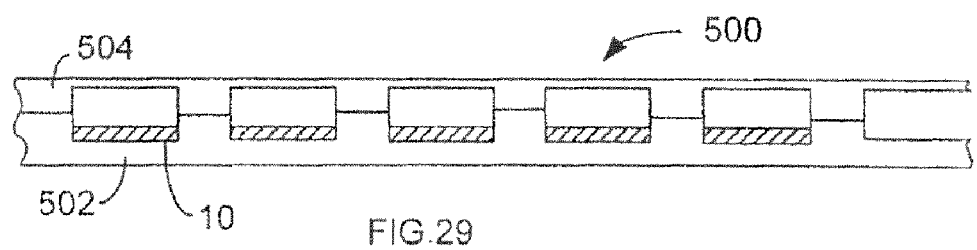
FIG. 29 is a schematic cross-sectional view of one preferred embodiment of the emitter device according to the present invention, showing a device employing an array of emitter devices.

According to a further aspect of the present invention, an emitter device assembly may include an array of the emitter devices 10 (or other embodiments as described above). FIG. 29 schematically illustrates an emitter/detector assembly 500 (the figure shows part of the assembly), which includes an array of the devices 10. As seen in FIG. 29, the assembly 500 includes a substrate 502 and a covering 504. In a preferred form, the array of devices 10 are addressable individually or in groups. For example, each device 10 may include electrical conductors extending through the substrate 504 and are connected to an external power source and/or a controller such that the each device 10 can be individually powered and, or controlled. The emitter/detector assembly 500 may be used in sensing or imaging systems.

Figure 30:
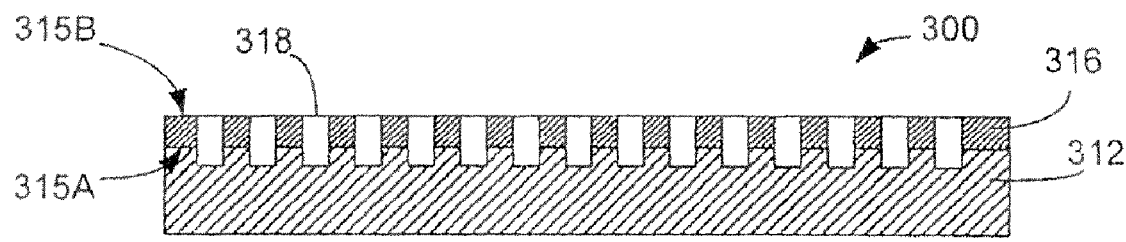
FIG. 30 schematically shows an infrared spectral shifting device according to one preferred embodiment of the present invention.

The present invention further provides an infrared spectral shifting (ISS) device 300 as shown in FIG. 30, which includes a dielectric material layer, preferably a plastic material layer (polymer) 312, and a metallic (or metallic like) material layer 316 overlaying the plastic material layer. The metallic layer 316 includes an inner surface 315A and an outer surface 315B. The inner surface 315A is the surface in contact with the plastic material layer 312. The metallic layer 316 includes periodically distributed surface features 318 on the outer surface 315B. The configurations of the periodically distributed surface features 318 including the size, shape, depth, spacing, and distribution geometry can be the same as in the embodiments described above. For example, the surface features can be holes defined through the metallic material layer 316 or holes defined through the metallic and plastic material layers 316 and 312.

Figure 31:
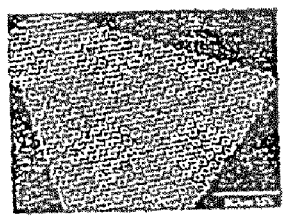
FIG. 31 schematically shows the infrared spectral shifting device in a form of a flexible sheet.
Figure 32:
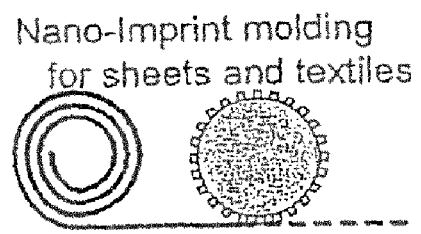
FIG. 32 schematically shows a system for making the infrared spectral shifting device in FIG. 31.
Figure 33:
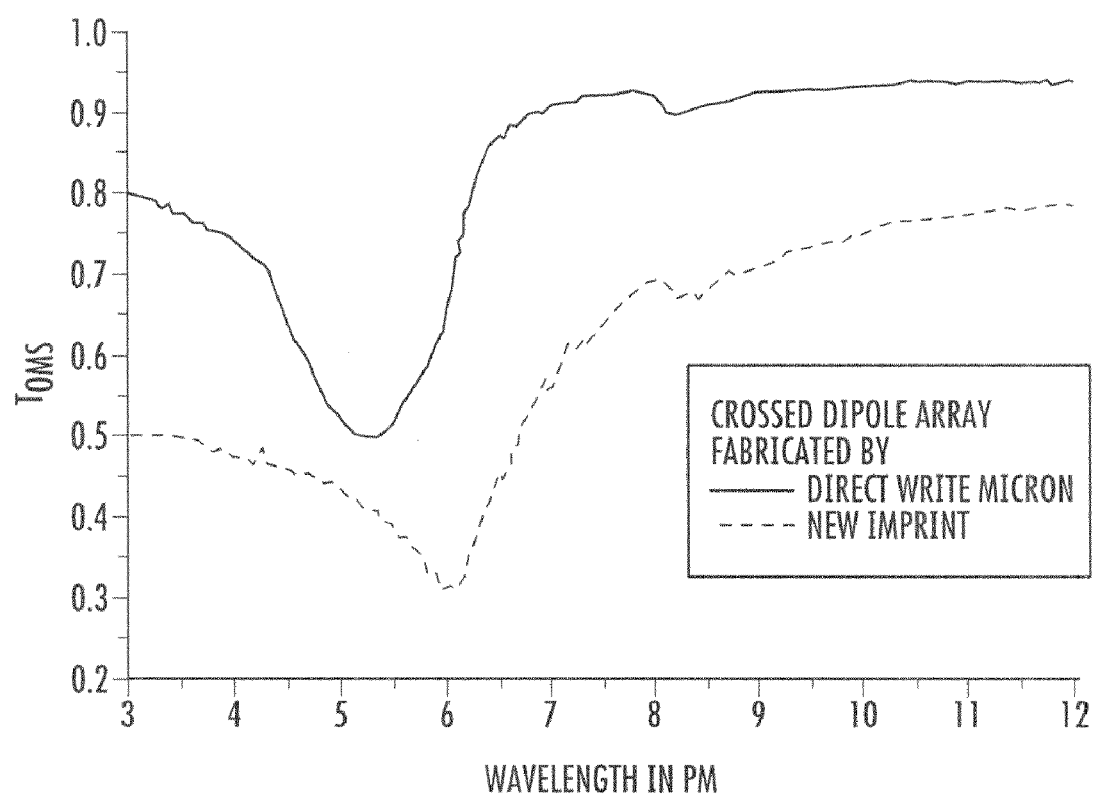
FIG. 33 shows a diagram of spectral characteristics of two infrared spectral shifting devices manufactured by different processes.

In the embodiment described above because a plastic material can be constructed with a flexible spread sheet, the emitter/absorber device according to the present invention can be made as a large flexible sheet, as shown in FIG. 31. FIG. 32 illustrates a schematic view of a nano-imprint molding system for defining the surface features on the flexible sheet of the device. The surface features also can be fabricated by UV lithography or by direct write e-beam technique. FIG. 33 shows the performance of the devices fabricated by the two different processes. As seen in FIG. 33, both curves show resonance. The flexible sheet with periodically distributed surface features thereon may be manufactured with other processes. Similar to the embodiments described above, the location and the bandwidth of the peak emission or absorption and the allowed band of transmission or reflection of the flexible large sheet emitter/absorber can be tuned by adjusting the surface feature configuration including the shape, size, periodicity, distribution geometry and defects. The flexible large sheet emitter/absorber device has many applications. For example, the device can be tuned to suppress infrared output in the bands where thermal imaging cameras operate. For another example, the device can be tuned to allow transmission of infrared wavelengths in the atmospheric water absorption bands and suppress infrared output in the adjacent bands.

Self Assembly: FIGS. 34A-34D briefly illustrate an alternative method, which is a self assembly process, for producing the periodically distributed surface features according to one preferred form of the present invention. First, a monolayer of microspheres is deposited on a top surface of the multiple layer structure of the emitter device, as shown in FIG. 34A. The microspheres are attached to the top surface of the device through electrostatic or covalent attachment. Then a polymer is added to form a negative template of the design as shown in FIG. 34B. The microspheres are removed by etching (developing) as shown in FIG. 34C. Next step is to transfer the pattern to the substrate by reactive ion etching as shown in FIG. 34D. This is followed by removal of the polymer template resist (not shown). The resulting surface has a regular hexagonal array of surface features that act as a two-dimensional photonic crystal. The self assembly process is further described in detail in the following paragraphs.

The self assembly technique employs a two dimensional colloidal crystal as a pattern template and imprints that pattern into a resist material. A fundamental requirement for such a strategy is a built-in driving force for the assembly of the colloid onto the surface. This diving force can be as simple as an electrostatic attraction between the colloid and the substrate. Through material selection such an electrostatic attraction is easily attainable. Monodisperse silica microspheres are now available from various companies (Duke Scientific, GelTech) both in solution and iii bulk as dried solids. When dispersed in neutral pH water, silica particles are negatively charged since the isoelectric point of $SiO_2$ is 2. This in turn requires a positively charged substrate which can be induced on alumina surfaces by simply immersing them in aqueous solutions with a pH well below the isoelectric point of $Al_2O_3$, which is equal to 9. This will work for both sapphire and aluminum (since aluminum always has a thin native oxide on the surface) at a pH of 5-7, an environment ideally suited for negatively charged silica panicles. An alternative substrate is freshly cleaved mica that has been ion exchanged with magnesium ions. The divalent $Mg^{2+}$ leaves net positive charge on the surface for attachment. This method has been extensively used in the atomic force microscopy community as a method to deposit negatively charged samples onto a surface for AFM analysis.

The deposition of the silica colloid onto the surface can be carried out by two methods. Dip coating is one of the two approaches. A monolayer of the colloid adhered to the surface as the substrate is drawn out of the suspension. The substrate is then coated with 2D colloidal crystals.

Dip coating is clearly a cheap and simple process, however, using a conventional semiconductor processing technique makes the process more easily integratable with standard fabrication techniques. Therefore spin coating is also an attractive method since it is the primary deposition technique for resists and organic passivation layers. The spinning process begins with depositing a few drops of the suspension onto the substrate which is already mounted on the spinner chuck. The suspension is allowed to sit on the surface for a short while to allow the substrate to come to equilibrium with the water. Then the system is spun at a low RPM in order to spin away the excess slurry while depositing only one monolayer.

In order for such a process to be viable on a production scale, the rate of deposition must be very fast. Therefore in an attempt to speedup the rate of deposition, alternative absorption chemistries may be necessary. The development of these alternative chemistries requires a robust system of reagents. These molecular systems were extensively investigated using alkane thiols on gold. Essentially self assembled monolayers form through the chemisorption of single functionality alkane based molecules onto a surface. The thiol functionality readily reacts with atomic gold, covalently linking the alkane chain to the gold surface. Once all available sites on the gold surface have reacted the system self passivates and the reaction stops. This results in a conformal coating of alkane chains onto the surface. This technology was extended to silicon and silicon dioxide surfaces through the discovery of alkane trichlorosilanes. These molecules react to the surface of Si or $SiO_2$ forming a self assembled monolayer (SAM). By mixing small percentages of divalent monomers to the SAM solution it is possible to generate surfaces with controlled functionality. By varying the concentration of divalent vs. monovalent monomers in the solution a user can linearly control the final surface density of functional groups. Currently divalent alkane thiols and trichlorosilanes are available from Aldrich in a variety of lengths. Therefore, by mixing monodisperse glass microbeads with a SAM solution of mono and divalent monomers a user can generate a controlled density of reactive groups on the silica spheres. These reactive groups will then have the capability to covalently link the silica colloidal particles to a glass or silicon surface. By controlling the divalent concentration, a user can dial in the chemisorptive potential of the microspheres for the substrate surface. In order to coat the substrate, a fast dipping method is required.

The SAM approach described above yields a system in which the colloidal particles are bound to the substrate through a direct covalent linkage. The ability to control the strength of the absorption (through variations in the number of covalent bonds) may prove useful in controlling the crystallization of the colloidal particles. When the absorption is too strong, then the particles are not free to migrate along the surface in search of a low energy lattice site. This in turn results in a randomly packed surface with no crystalline periodicity. By reducing the absorption energy the colloidal particles are more free to explore different sites on the surface. In doing so the system can more easily achieve the desired crystalline packing.

In order to directly copy the symmetry and periodicity of the colloidal assembly, a direct templating methodology is used. A templating technique can be effectively carried out on an inverse system, i.e. using a soft organic hexagonal lattice to template a rigid inorganic phase. A fluid polymer precursor to infiltrate the lattice filling up the interstitial voids is used. This polymerizable liquid can be either urethane, styrene or methylmethacrylate (Aldrich). Capillary forces are enormous in the 1-2 micron size regime and therefore will strongly draw the fluid into the void spaces between neighboring microspheres. Once the system has completely filled all of the interstitial sites, UV radiation is applied to polymerize the resist, fixing it in place. Now by dissolving the silica out of the structure with hydrofluoric acid, the pattern is "developed" in the resist. The final structure will appear as a hexagonal array of dimples in a polymer film. At the bottom of each dimple the substrate is exposed where the microsphere touched the substrate. It will be through this hole that pattern transfer to the substrate can occur by reactive ion etching or wet chemical etching. This results in a direct copy of the symmetry and periodicity of the original colloidal template onto the substrate surface.

Figure 35:
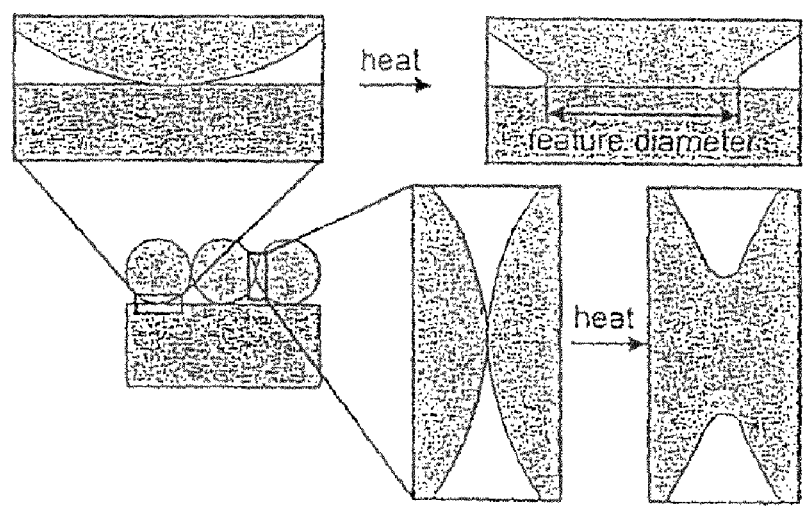
FIG. 35 schematically shows an annealing process according to one preferred embodiment of the present invention.

A powerful corollary to this methodology is control of the feature size. Once the colloid has been deposited onto the surface, the system can be annealed. During this annealing process the colloidal particles will sinter together. They will also sinter to the surface of the substrate as shown in FIG. 35. The time and temperature of the anneal defines the radius of the sintering cross section. This sintering cross section will manifest itself as the size of the hole after templating thus providing an avenue to control the feature dimensions as well as the periodicity and symmetry. This sintering technique has been already investigated in three dimensional colloidal structures.

Spin coating a low concentration solution of resist might also be an effective pattern transfer methodology. If the concentration is low enough such that the coating thickness is well below the thickness of the 2D array then it should be possible to deposit a conformal coating in the interstitial sites of the lattice. Then after an HF etch of the silica, a thin patterned resist remains. The advantage of such a technique is that the methodology does not deviate drastically from conventional semiconductor processing. This is important for developing a working fabrication process that is manufacturable.

For a MEMS device embodying the present invention, the manufacturing process flow must integrate all of the elements of MEMS processing technology including both low and high resolution lithography steps, release etching and deep trenches. Using the proposed patterning technique the devices will be fabricated following the guidelines shown in FIG. 36. The process begins with silicon SOI (semiconductor on insulator) wafers. Silicon nitride is deposited by PECVD to a thickness of 150 nm. Etch through vias are drilled into the nitride film revealing the top silicon surface. Metal is deposited onto the substrate using a conventional lift off method. Next, the wafer is dip coated in a colloidal suspension. The colloidal crystal is then templated and after development the substrate can be etched using reactive ion etching or wet chemical methods to create the photonic band gap surface structure. The infrared filament is then cut out of the top silicon by deep RIE. This reveals the embedded sacrificial oxide layer which can then be under-etched to release the filament. This is canned out in buffered HF which has a strong selectivity for silicon oxide. Finally critical point drying is used to dry the sample and prevent stiction of the bridge filament to the base silicon. The device will then be mounted in a TO-8 transistor can, wire bonded, and tested.

Sense Element: According to another aspect of the present invention a separate, integrated sense element is incorporated onto the emitter device. The sense element is of any material that couples temperature change or photon density to changes in resistance, capacitance, polarization mechanical resonance, carrier type, magnetic properties, Hall effect, depletion width, phonon states, carrier lifetime or photocurrent. The sense element is made from a material preferably selected from but not limited to a group including ferroelectrics, piezoelectrics, metal oxides, metal nitrides, and ceramic materials. According to a further aspect of the present invention, the detector device embodying the present invention employs a measurement mechanism using a transistor or a diode.

According to another aspect of the present invention, the emitter device further includes a heater for heating the multilayer emitter. In one preferred form, the heater is a layer of material mounted on the emitter. In another preferred form, the heater and the emitter are separate elements in the same plane of the device. In a further form, the heater and the emitter are separate elements in different planes of the device.

While the claimed invention has been described in detail and with reference to specific embodiments thereof, it will be apparent to one of ordinary skill in the art that various changes and modifications can be made to the claimed invention without departing from the spirit and scope thereof. Thus, for example those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A photonic crystal device comprising:
    a semiconductor material layer capable of being coupled to an energy source for introducing energy to said semiconductor material layer;
    a dielectric material layer overlaying the semiconductor material layer; and
    a conductive material layer overlaying the dielectric material layer, and including periodically distributed surface features,
wherein the device is adapted to emit and/or absorb electromagnetic energy having spectral characteristics determined at least in part by parameters of said periodically distributed surface features, wherein the periodically distributed surface features comprise an array of holes, and holes individually extending through at least a portion of the conductive material layer, and wherein said holes are at least partially filled with a material selected from a group consisting of a dielectric material, a non-linear optical material, a liquid crystal material, a piezoelectric material, a pyroelectric material, and a ferroelectric material; and
    wherein the device is characterized by at least one feature from the list consisting of:
    a) said periodically distributed surface features are distributed in a geometry selected from a group of regular geometry distributions consisting of parallelogram and hexagon, and quasi-regular geometry distributions consisting of Archimedean tiling,
    b) said conductive layer is biased with a voltage, and wherein said spectral characteristics of said electromagnetic energy is determined by said voltage, and
    c) said periodically distributed surface features include distributed defects which comprise a first portion said surface features which are structurally different from a second portion of said surface features.

2. A device according to claim 1, wherein said holes have a shape selected from the group consisting of circle, n-point star, square, triangle, hexagon, donut, C and reverse C, rectangle, circle with a notch, triple-leg, and tri-bone.

3. A device according to claim 1, wherein said periodically distributed surface features are distributed in a geometry selected from a group of regular geometry distributions consisting of parallelogram and hexagon, and quasi-regular geometry distributions consisting of Archimedean tiling.

4. A device according to claim 1, wherein the holes individually extend through the metallic material layer and at least a portion of the dielectric material layer.

5. A device according to claim 4, wherein the holes individually extend through the dielectric material layer and at least a portion of the semiconductor material layer.

6. A device according to claim 1, wherein the holes individually extend through the conductive material layer, the dielectric material layer, and the semiconductor material layer.

7. A device according to claim 1, wherein said semiconductor layer comprises a material selected from a group consisting of single-crystal silicon, polysilicon, single-crystal silicon carbide, polycrystalline silicon carbide, germanium, the group III-V semiconductors, and the group II-VI semiconductors, and semiconductors plastics and small molecule semiconducting organics.

8. A device according to claim 1, wherein said dielectric material layer comprises a dielectric material selected from the group consisting of silicon dioxide, silicon nitride, alumina, sapphire, aluminum nitride, silicon oxinitride, and plastic.

9. A device according to claim 1, wherein said conductive material layer comprises a metal selected from the group consisting of gold, aluminum, nickel, silver, titanium, tantalum, platinum, and a heavily doped semiconductor.

10. A device according to claim 1, wherein said conductive material layer comprises a conductive ceramic selected from the group consisting of titanium nitride, tantalum nitride and indium tin oxide.

11. A device according to claim 1, wherein said conductive material layer is biased with a voltage, and wherein said spectral characteristics of said electromagnetic energy is determined by said voltage.

12. A device according to claim 1, wherein said semiconductor material layer is biased with a voltage, and wherein said spectral characteristics of said electromagnetic energy is determined by said voltage.

13. A device according to claim 1, wherein said periodically distributed surface features include distributed defects, which comprise a first portion said surface features which are structurally different from a second portion of said surface features.

14. A device according to claim 13 wherein said distributed defects are periodically distributed.

15. A device according to claim 14, wherein said periodically distributed defects occur at positions of every third surface feature.

16. A photonic crystal device comprising:
    a semiconductor material layer capable of being coupled to an energy source for introducing energy to said semiconductor material layer;
    a dielectric material layer overlaying the semiconductor material layer; and
    a conductive material layer overlaying the dielectric material layer, and including periodically distributed surface features,
wherein the device is adapted to emit and detect electromagnetic energy having spectral characteristics determined at least in part by parameters of said periodically distributed surface features, wherein the periodically distributed surface features comprise an array of holes and the holes individually extend through the conductive material layer, said dielectric layer and said semiconductor layer;

wherein said periodically distributed surface features are distributed in a geometry selected from a group of regular geometry distributions consisting of parallelogram and hexagon and quasi-regular geometry distributions consisting of Archimedean tiling.

17. A device according to claim 16, wherein said holes have a shape selected from the group consisting of circle, n-point star, square, triangle, hexagon, donut, C and reverse C, rectangle, circle with a notch, triple-leg, and tri-bone.

18. A device according to claim 16, wherein said conductive material layer is biased with a voltage, and wherein said spectral characteristics of said electromagnetic energy is determined by said voltage.

19. A device according to claim 16, wherein said semiconductor material layer is biased with a voltage, and wherein said spectral characteristics of said electromagnetic energy is determined by said voltage.

20. A photonic crystal device comprising:
   a semiconductor material layer capable of being coupled to an energy source for introducing energy to said semiconductor material layer;
   a dielectric material layer overlaying the semiconductor material layer; and
   a conductive material layer overlaying the dielectric material layer, and including periodically distributed surface features, wherein the device is adapted to emit and/or absorb electromagnetic energy, having said emitted electromagnetic energy has spectral characteristics determined at least in part by parameters of said periodically distributed surface features, said parameters including shape, size, depth, distribution geometry, and periodicity;
wherein said surface features have a shape selected from the group consisting of circle, triangle, annulus, C and reverse C, circle with a notch, triple-leg, and tri-bone;
   wherein the device is characterized by at least one feature from the list consisting of:
   a) the periodically distributed surface features comprise an array of holes and the holes individually extend through at least a portion of the conductive material layer, wherein the periodically distributed surface features comprise an array of protrusions extending from said conductive material layer, and
   b) said periodically distributed surface features are distributed in a geometry selected from a group or regular geometry distributions consisting of parallelogram and hexagon and quasi-regular geometry distributions consisting of Archimedean tiling.

21. A device according to claim 20, wherein the periodically distributed surface features comprise an array of holes and the holes individually extend through at least a portion of the conductive material layer.

22. A device according to claim 21, the periodically distributed surface features comprise an array of protrusions extending from said conductive layer.

23. A device according to claim 20, wherein said periodically distributed surface features are distributed in a geometry selected from a group or regular geometry distributions consisting of parallelogram and hexagon and quasi-regular geometry distributions consisting of Archimedean tiling.

24. A device according to claim 20, wherein said conductive material layer is biased with a voltage, and wherein said spectral characteristics of said electromagnetic energy is determined by said voltage.

25. A device according to claim 20, wherein said semiconductor material layer is biased with a voltage, and wherein said spectral characteristics of said electromagnetic energy is determined by said voltage.

26. A photonic crystal comprising:
   a semiconductor material layer capable of being coupled to an energy source for introducing energy to said semiconductor material layer;
   a dielectric material layer overlaying the semiconductor material layer; and
   a conductive material layer overlaying the dielectric material layer, and including periodically distributed surface features, wherein the device is adapted to emit and/or absorb electromagnetic energy having spectral characteristics determined at least in part by parameters of said periodically distributed surface features,
wherein the periodically distributed surface features comprises an array of holes and the holes individually extend through at least a portion of the conductive material layer, wherein said semiconductor material layer includes an array of holes extending at least partially therethrough;
   wherein said holes in said metallic material layer and said holes in said semiconductor layer each extend along mutually parallel axes;
   and wherein the device is characterized by at least one feature from the list consisting of:
   a) said axes of said holes of said conductive material layer and said axes of said holes of said semiconductor material layer are coaxial,
   b) said axes of said holes of said conductive material layer and said axes of said holes of said semiconductor material layer are axially offset, and
   c) said holes of said conductive material layer and said holes of said semiconductor material layer have different geometry.

27. A device according to claim 26 wherein said axes of said holes of said conductive material layer and said axes of said holes of said semiconductor material layer are coaxial.

28. A device according to claim 26 wherein said axes of said holes of said conductive material layer and said axes of said holes of said semiconductor material layer are axially offset.

29. A device according to claim 26 wherein said holes of said conductive material layer and said holes of said semiconductor material layer have the different geometry.

30. A device according to claim 26, wherein said conductive material layer is biased with a voltage, and wherein said spectral characteristics of said electromagnetic energy is determined by said voltage.

31. A device according to claim 26, wherein said semiconductor material layer is biased with a voltage, and wherein said spectral characteristics of said electromagnetic energy is determined by said voltage.

32. A photonic crystal device comprising:
   a semiconductor material layer capable of being coupled to an energy source for introducing energy to said semiconductor material layer;
   a dielectric material layer overlaying the semiconductor material layer; and
   a conductive material layer overlaying the dielectric material layer, and including periodically distributed surface features,
wherein the device is adapted to emit and/or absorb electromagnetic energy having spectral characteristics determined at least in part by parameters of said periodically distributed surface features, wherein the periodically distributed surface features comprise an array of holes, and holes individually extending through at least a portion of the conductive material layer, and wherein said holes are at least partially filled with a material selected from a group consisting of a dielectric material, a non-linear optical material, a liquid crystal material, a piezoelectric material, a pyroelectric material, and a ferroelectric material; and wherein said conductive material layer comprises a metal selected from the group consisting of gold, aluminum, nickel, silver, titanium, tantalum, platinum, and a heavily doped semiconductor.

33. A device according to claim 32, wherein said conductive material layer is biased with a voltage, and wherein said spectral characteristics of said electromagnetic energy is determined by said voltage.

34. A device according to claim 32, wherein said semiconductor material layer is biased with a voltage, and wherein said spectral characteristics of said electromagnetic energy is determined by said voltage.

35. A device according to claim 32, wherein said conductive material layer is biased with a voltage, and wherein said spectral characteristics of said electromagnetic energy is determined by said voltage.

36. A device according to claim 32, wherein said semiconductor material layer is biased with a voltage, and wherein said spectral characteristics of said electromagnetic energy is determined by said voltage.

37. A photonic crystal device comprising:

a semiconductor material layer capable of being coupled to an energy source for introducing energy to said semiconductor material layer;

a dielectric material layer overlaying the semiconductor material layer; and a conductive material layer overlaying the dielectric material layer, and including periodically distributed surface features, wherein the device is adapted to emit and/or absorb electromagnetic energy having spectral characteristics determined at least in part by parameters of said periodically distributed surface features, wherein the periodically distributed surface features comprise an array of holes, and holes individually extending through at least a portion of the conductive material layer, and wherein said holes are at least partially filled with a material selected from a group consisting of a dielectric material, a non-linear optical material, a liquid crystal material, a piezoelectric material, a pyroelectric material, and a ferroelectric material; and wherein said conductive material layer comprises a conductive ceramic selected from the group consisting of titanium nitride, tantalum nitride and indium tin oxide.

* * * * *